US009388444B2

(12) United States Patent
Solaiman et al.

(10) Patent No.: US 9,388,444 B2
(45) Date of Patent: Jul. 12, 2016

(54) USE OF GLUCOSYLTRANSFERASE GENE

(71) Applicant: The United States of America, as represented by the Secretary of Agriculture, Washington, DC (US)

(72) Inventors: Daniel K Solaiman, Dresher, PA (US); Richard D Ashby, Glenside, PA (US); Jonathan A. Zerkowski, Lexington, MA (US); Robert A Moreau, Quakertown, PA (US); Yanhong Liu, Warrington, PA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/695,236

(22) Filed: Apr. 24, 2015

(65) Prior Publication Data
US 2015/0267236 A1 Sep. 24, 2015

Related U.S. Application Data

(62) Division of application No. 13/773,993, filed on Feb. 22, 2013, now abandoned.

(51) Int. Cl.
| | |
|---|---|
| *C12N 9/10* | (2006.01) |
| *C12P 21/06* | (2006.01) |
| *C12P 19/34* | (2006.01) |
| *C12N 1/20* | (2006.01) |
| *C12N 1/00* | (2006.01) |
| *C12N 5/07* | (2010.01) |
| *C07H 21/04* | (2006.01) |
| *C07K 1/00* | (2006.01) |
| *C12P 19/44* | (2006.01) |
| *C12P 19/18* | (2006.01) |
| *C12P 33/00* | (2006.01) |

(52) U.S. Cl.
CPC .............. *C12P 19/44* (2013.01); *C12N 9/1051* (2013.01); *C12P 19/18* (2013.01); *C12P 33/00* (2013.01); *C12Y 204/01017* (2013.01); *Y02P 20/52* (2015.11)

(58) Field of Classification Search
CPC .......... C12P 19/44; C12P 33/00; C12P 19/18; C12N 9/1051; Y02P 20/52; C12Y 204/01017
USPC ......... 435/74, 193, 69.1, 91.1, 252.3, 254.11, 435/348; 536/23.1, 23.2; 530/350
See application file for complete search history.

(56) References Cited

U.S. PATENT DOCUMENTS

| | | | |
|---|---|---|---|
| 7,439,049 B2 | 10/2008 | Bozonet et al. | |
| 2004/0053834 A1 | 3/2004 | Lal et al. | |

OTHER PUBLICATIONS

Argimon et al., "Phylogenetic Analysis of Glucosyltransferases and Implications for the Coevolution of *mutans Streptococci* with their Mammalian Hosts", (2013) PLOS ONE. 8: e56305, 1-11.
Breithaupt, T.B. et al., "Affinity Chromatography and Further Characterization of the Glucosyltransferases Involved in Hydroxydocosanoic Acid Sophoroside Production in Candida Bogoriensis", (1982) The Journal of Biological Chemistry, 257(16):9622-9628.
Cutler, A.J. et al., "Regulation of Hydroxydocosanoic Acid Sophoroside Production in Candida Bogoriensis by the Levels of Glucose and Yeast Extract in the Gro'Nth Medium", (1978) Journal of Biological Chemistry 254(6):1944-1950.
Cutler, A.J. et al. "Effect of Glucose Concentration in the Gro'Nth Medium on the Synthesis of Fatty Acids by the Yeast Candida Bogoriensis", (1982) Can. J. Microbiol. 28:223-230.
Esders, T.W. et al, "Glucosyl- and Acetyltransferases Involved in the Biosynthesis of Glycolipids from Candida Bogoriensis", (1972) The Journal of Biological Chemistry 247(5):1375-1385.
Esders, T.W. et al., Occurrence of a Uridine Diphosphate Glucose:Sterol Glucosyltransferase in Candida Bogoriensis, (1972) The Journal of Biological Chemistry 247(23):7494-7497.
Esders, T.W. et al., "Characterization and in vivo Production of Three Glycolipids from Candida Bogoriensis: 13-Glucopyranosylglucopyranosyloxydocosanoic Acid and its Mono- and Diacetylated Derivatives" (1972) Journal of Lipid Research 13:663-671.
Gen Bank: FJ231291.1, gene search, NCBI, 3 pages, downloaded from http://www.ncbi.nlm.nih.gov/ on Oct. 1, 2014.
Kasture, M. et al., "Multiutility Sophorolipids as Nanoparticle Capping Agents: Synthesis of Stable and Water Dispersible Co Nanoparitcles", (2007) Langmuir 23:11409-11412.
Kim, K. et al., "Characteristics of Sophorolipid as an Antimicrobial Agent", (2002) Journal Microbiology Biotechnology 12(2):235-241.
Konishi, M. et al., "Structure and Enzymatic Properties of Genetically Truncated Forms of the Water-Insoluble Glucan-Synthesizing Glucosyltransferase from *Streptococcus sobrinus*" (1999) J. Biochem. 126:287-295.
Konishi, M. et al., "Production of New Types of Sophorolipids by Candida Batistae", (2008) Journal of Oleo Science . 57(6):359-369.
Kost et al., "Baculovirus as versatile vectors for protein expression in insect and mammalian cells", (2005) Nat Biotechnology, 2005, vol. 23 (5): 567-575.
Nitschke, M. et al., "Biosurfactants in Food Industry", (2007) Trends in Food Science & Technology 18:252-259.
Nunez, A. et al., "LC/MS Analysis and Lipase Modification of the Sophorolipids Produced by Rhodotorula Bogoriensis", (2004) Biotechnology Letters 26:1087-1093.
Rau, U. et al., "Sophorolipids: A Source for Novel Compounds", (2001) Industrial Crops and Products 13:85-92.
Ribeiro, I.A. et al., "Optimization and Correlation of HPLC-ELSD and HPLC-MS/MS Methods for Identification and Characterization of Sophorolipids", (2012) Journal of Chromatography B 899:72-80.

(Continued)

*Primary Examiner* — Ganapathirama Raghu
(74) *Attorney, Agent, or Firm* — John D. fado; David L. Marks

(57) ABSTRACT

The isolation and characterization of a glucosyltransferase gene from *Candida bombicola* is disclosed. Use of the glucosyltransferase enzyme for the production of glucosylated sterol and hydroxyl-fatty acid substrates is also disclosed. This enzyme has broad-specificity and is useful for the production of sophorolipids both in-vivo and in-vitro.

11 Claims, 3 Drawing Sheets

(56) References Cited

OTHER PUBLICATIONS

Saerens, K.M.J. et al., "Identification of the UDP-Glucosyltransferase Gene UGTA1, Responsible for the First Glucosylation Steop in the Sophorolipid Biosynthetic Pathway of Candida Bombicola ATCC 22214", (2011) FEMS Yeast Res 11:123-132.

Saerens, K.M.J. et al., "Cloning and Functional Characterization of the UDP-Glucosyltransferase UgtB1 Involved in Sophorolipid Production by Candida Bombicola and Creation of a Glucolipid-Producing Yeast Strain", (2011) Yeast 28:279-292.

Seffernick et al., "Melamine Deaminase and Atrazine Chlorohydrolase: 98 Percent Identical but Functionally Different", (2001) Journal Bacteriology 183(8):2405-2410.

Shah, V. et al., "Sophorolipids, Microbial Glycolipids with Anti-Human Immunodeficiency Virus and Sperm Immobilizing Activities", (2005) Antimicrobial Agents and Chemotherapy 49(10):4093-4100.

Solaiman, D.K.Y. et al., "Production of Sophorolipids by Candida Bombicola Grown on Soy Molasses as Substrate", (2004) Biotechnolgy Letters 36:1241-1245.

Solaiman et al., "Cloning, characterization, and heterologous expression of a novel glucosyltransferase gene from sophorolipid-producing Candida bombicola", (2014) Gene 46-53.

Suto, M. et al., "Induction and Catabolite Repression Mechanisms of Cellulase in Fungi", (2001) Journal of Bioscience and Bioengeneering 92:305-311.

Van Bogaert, I.NA et al, "Microbial Production and Application of Sohporolipids", (2007) Applied Microbiology Biotechnology 76:23-24.

Van Bogaert, I.NA et al., "Knocking Out the MFE-2 Gene of Candida Bombicola Leads to Improved Medium-Chain Sophorolipid Production", (2009) FEMS Yeast Res. 9:610-617.

Van Bogaert, I.NA et al., "Microbial synthesis of sophorolipids", (2011) Process Biochemistry 46:821-833.

Whisstock et al., "Prediction of protein function from protein sequence and structure", (2003) Quart. Rev. BioPhys 36:307-340.

Witkowski et al., "Conversion of a 13-Ketoacyl Synthase to a Malonyl Decarboxylase by Replacement of the Active-Site Cysteine with Glutamine", (1999) Biochemistry 38:11643-11650.

Zerkowski, J.A. et al., :Synthesis of Polyfunctional Fatty Amines from Sophorolipid-Derived 17-Hydrowy Oleic Acid:, (2006) Journal of the American Oil Chemists' Society 83(7):621-628.

Zerkowski, J.A. et al., "Polyhydroxy Fatty Acids Derived from Sophorolipid", (2007) Journal of the American Oil Chemists' Society 84:463-471.

USE OF GLUCOSYLTRANSFERASE GENE

This patent application is a divisional patent application of and claims priority to U.S. patent application Ser. No. 13/773,993 filed on Feb. 22, 2013 which is abandoned.

BACKGROUND OF THE INVENTION

1. Field of the Invention

This invention relates to the use of a glucosyltransferase gene in recombinant cells to produce a precursor of sophorolipid and of phytosteryl glucosides.

2. Description of the Prior Art

Sophorolipid is a glycolipid produced and secreted by several yeast species such as *Candida apicola*, *C. bombicola*, *Rhodotorula bogoriensis*, *Starmerella bombicola*, *Wickerhamiella domericqiae*, and *C. batistae* (see, Van Bogaert, et al. 2007. *Appl. Microbiol. Biotechnol.* 76:23-34; and Konishi, et al. 2008. *J. Oleo Sci.* 57:359-369). Sophorolipid contains a hydrophilic disaccharide sophorose (2-O-β-D-glucopyranosyl-β-D-glucopyranose), which may or may not be enzymatically acetylated in vivo at the 6'-(C-6') or both C-6' and C-6". The hydrophobic portion of the molecule contains a hydroxy fatty acid, which is glycosidically linked to the C-2' of the sophorose moiety. In this respect, sophorolipid differentiates itself from the synthetic alkylpolyglucosides which have an ester bond between the hydrophobic and hydrophilic moieties of the molecule. The carboxyl group of the hydroxy fatty acid moiety of sophorolipid may also be found esterified in vivo to the C-4" of the sophorose, resulting in a lactone structure of the molecule. The proportion of the various forms of sophorolipid produced from a particular fermentation depends to certain degree on the yeast strain used, the fermentation substrates, and the growth conditions. It should be noted that *R. bogoriensis* produces sophorolipid containing mainly a 13-hydroxydocosanoic acid (13-OH—C22) moiety (see Esders and Light 1972. *J. Lipid Res.* 13:636-671; Nuñez, et al. 2004. *Biotechnol. Lett.* 26:1087-1093; and Ribeiro, et al. 2012. *J. Chromatogr. B* 899:72-80), while the other sophorolipid-producing yeast strains predominantly synthesize the glycolipid having a 17-hydroxyoctadecenoic acid (17-OH—C18:1) as its hydrophobic component. The structural versatility of sophorolipid affords the possibility of designing specific production systems to tailor make products suitably targeted for an intended application.

Sophorolipid is an important microbial product with immense potential for industrial applications (Solaiman, et al. 2004a. *Informs* 15:270-272). Its amphiphatic structure bestows an excellent surface-active property to the molecule. Surface-tension measurements of an aqueous solution of sophorolipid routinely yielded values of 30-40 mN/m (see, for example, Solaiman, et al. 2004b. *Biotechnol. Lett.* 26:1241-1245). The antimicrobial activity and various biomedical properties of sophorolipid have been extensively documented (Hardin, et al. 2007. *J. Surg. Res.* 142:314-319; Kim, et al. 2005. *J. Microbiol. Biotechnol.* 15:55-58; Kim, et al. 2002. *J. Microbiol. Biotechnol.* 12:235-241, Krivobok, et al. 1994. *J. Agric. Food Chem.* 42:1247-1250; Lang, et al. 1989. *Fett Wiss. Technol.* 91:363-366; and Shah, et al. 2005. *Antimicrob. Agents Chemother.* 49:4093-4100). The potential applications of sophorolipid in the food-industry arena, such as its use as a formulation ingredient to modulate the rheological and textural properties and as an inhibitor of biofilm-formation by food pathogens, have been proposed (Nitschke and Costa 2007. *Trends Food Sci. Technol.* 18:252-259). Kasture et al. (*Langmuir* 23:11409-11412) recently showcased the value of sophorolipid in the field of nanotechnology by demonstrating its use in the capping of cobalt nanoparticles, thereby improving its water stability and dispersive property. The individual structural components of sophorolipid, i.e., the sophorose (Suto and Tomita 2001. *J. Biosci. Bioeng.* 92:305-311) and the hydroxy fatty acid (Zerkowski and Solaiman 2006. *J. Am. Oil Chemists' Soc.* 83:621-628; Zerkowski and Solaiman 2007. *J. Am. Oil Chemists' Soc.* 84:463-471), are also valuable specialty chemicals when separated and isolated (Rau, et al. 2001. *Ind. Crops Prod.* 13:85-92).

With a myriad of potential applications envisioned and the high commercial value expected of the sophorolipid, research and development efforts have largely been aimed at increasing the production yield and reducing the cost of this glycolipid. In comparison, fundamental research to delineate the metabolic pathway and the genetics of sophorolipid biosynthesis is lacking. A notable exception is a series of pioneering studies on the enzymology of sophorolipid biosynthesis of *R. bogoriensis* (formerly *Candida bogoriensis*) conducted by Esders, Light and collaborators. They first identified two glucosyl- and one acetyl-transferase activities in *R. bogoriensis* (Esders and Light, 1972a. *J. Biol. Chem.* 247:1375-1386). The two glucosyltransferase activities (i.e., glucosyltransferases 1 and 2), which resisted various chromatographic attempts to separate them, catalyze the sequential addition of glucose units to 13-hydroxydocosanoic acid to form the final sophorolipid molecule by utilizing UDP-glucose as substrate (Breithaupt and Light, 1982. *J. Biol. Chem.* 257:9622-9628; Esders and Light, 1972a). An UDP-glucose:sterol glucosyltransferase, which catalyzes the transfer of the activated glucosyl group to ergosterol (an indigenous substrate) and cholesterol, was also identified in the course of their studies (Esders and Light, 1972b. *J. Biol. Chem.* 247:7494-7497). These investigators further identified an acetyltransferase activity that catalyzes the transfer of an acetyl group from acetyl coenzyme A (acetyl-CoA) to a mono- or un-acetylated sophorolipid (Esders and Light 1972a). The enzyme exhibited low reactivity toward mono-glucopyranosyl-13-hydroxydocosanote substrate. This finding, coupled with the observation that the acetyltransferase activity only peaked at a later time of fermentation, suggested that the acetylation of sophorolipid occurred mainly after the complete synthesis of the di-glucopyranosyl-13-hydroxydocosanoate. Cutler and Light (Cutler and Light, 1979. *J. Biol. Chem.* 254:1944-1950; and Cutler and Light, 1982. *Can. J. Microbiol.* 28:223-230) reported that a low concentration of glucose substrate led to diminished glucosyltransferase activities, and a high glucose concentration was necessary for the synthesis of fatty acids having 20- and 22-carbon chain length found in sophorolipid of *R. bogoriensis*. Although the enzymatic aspect of sophorolipid biosynthesis in *R. bogoriensis* was well-illustrated by this earlier elegant research in Light's laboratory, the probable sophorolipid biosynthesis pathway of *C. bombicola* is only beginning to emerge through a series of recent molecular biological studies (Saerens et al. 2011a. *FEMS Yeast Res.* 11:123-132; Saerens et al. 2011b. *Yeast* 28:279-292; and Van Bogaert et al. 2009. *FEMS Yeast Res.* 9:610-617). Saerens et al. 2011a reported the identification of a glucosyltransferase gene, UGTA1, in *C. bombicola*. Through knocking-out the UGTA1 in *C. bombicola*, it was shown that sophorolipid synthesis was not detected (Saerens et al. 2011a). The enzymatic function of the UGTA1 gene, however, was not confirmed by a direct biochemical assay in the same way as the Gtf-1 gene-product in this invention. Thus the inability of UGTA1 knock-out mutant to synthesize sophorolipid could not be conclusively attributed to the absence of glucosyltransferase activity in the first step of the biosynthesis pathway of sophorolipids.

While elucidating the genetic system of sophorolipid biosynthesis in *C. bombicola*, the cloning of a lipid-glucosyltransferase gene (gtf-1) from *C. bombicola* occurred, and the DNA sequence was published (GenBank Accession FJ231291.1). The DNA sequence of gft-1 differs from the other known yeast and fungal glucosyltransferases, including those identified recently in *C. bombicola* (Saerens, et al. 2011a; and Saerens, et al. 2011b. *Yeast* 28:279-292). However various uses of gtf-1 have not been disclosed until now.

BRIEF DESCRIPTION OF THE INVENTION

It is an object of this invention to have a recombinant cell containing a polynucleotide sequence encoding Gtf-1.

It is an object of this invention to have a recombinant cell containing a polynucleotide sequence encoding Gtf-1. It is a further object of this invention that the polynucleotide sequence encoding Gtf-1 is under control of either a constitutive promoter or an inducible promoter.

It is an object of this invention to have a recombinant cell containing a polynucleotide sequence encoding Gtf-1. It is a further object of this invention that the polynucleotide sequence encoding Gtf-1 is under control of either a constitutive promoter or an inducible promoter. It is another object of this invention that the recombinant cell is a fungus, bacterium or insect cell line.

It is an object of this invention to have a recombinant cell containing a polynucleotide sequence encoding Gtf-1. It is a further object of this invention that the polynucleotide sequence encoding Gtf-1 is under control of either a constitutive promoter or an inducible promoter. It is another object of this invention that the recombinant cell is a fungus, bacterium, or insect cell line. It is another object of this invention that the recombinant fungus is *Saccharomyces* spp, *Pichia* spp., or *Kluyveromyces* spp. It is a further object of this invention that the recombinant fungus is *S. cerevisiae, Pichia pastoris, Pichia methanolica*, or *luyveromyces lactis*. Alternatively, it is an object of this invention that the recombinant bacterium is *Escherichia coli, Bacillus subtilis*, or *Pseudomonas* spp. Alternatively, it is an object of this invention that the insect cell line is Sf9, Sf21, High Five, and S2.

It is an object of this invention to have a method of producing steryl glucosides and phytosteryl glucosides by culturing a recombinant cell containing the Gtf-1 gene with one or more sterols or one or more phytosteryl substrates and one or more sugar substrates.

It is an object of this invention to have a method of producing steryl glucosides and phytosteryl glucosides by culturing a recombinant cell containing the Gtf-1 gene with one or more sterols or one or more phytosteryl substrates and one or more sugar substrates. It is another object of this invention that the recombinant cell produces Gtf-1.

It is an object of this invention to have a method of producing steryl glucosides and phytosteryl glucosides by culturing a recombinant cell containing the Gtf-1 gene with one or more sterols or one or more phytosteryl substrates and one or more sugar substrates. It is another object of this invention that the recombinant cell produces Gtf-1. It is a further object of this invention that the recombinant cell is a fungus, bacterium, or insect cell line.

It is an object of this invention to have a method of producing steryl glucosides and phytosteryl glucosides by culturing a recombinant organism containing the Gtf-1 gene with one or more sterols or one or more phytosterol substrates and one or more sugar substrates and then isolating the produced steryl glucosides or phytosteryl glucosides. It is another object of this invention that the recombinant organism produces Gtf-1. It is a further object of this invention that the recombinant cell is a fungus, bacterium, or insect cell line. It is an even further object of this invention that the recombinant fungus is a *Saccharomyces* spp., *Pichia* spp., or *Kluyveromyces* spp.; and more specifically, *S. cerevisiae, Pichia pastoris, Pichia methanolica*, or *Kluyveromyces lactis*. Alternatively, it is an object of this invention that the recombinant bacterium is *Escherichia coli, Bacillus subtilis*, or *Pseudomonas* spp. Alternatively, it is an object of this invention that the insect cell line is Sf9, Sf21, High Five, and S2.

It is an object of this invention to have a method of producing steryl glucosides and phytosteryl glucosides by culturing a recombinant cell containing the Gtf-1 gene with one or more sterol substrates or one or more phytosterol substrates and one or more sugar substrates, and then isolating the produced steryl glucosides or phytosteryl glucosides. It is another object of this invention that the recombinant cell produces Gtf-1. It is a further object of this invention that the recombinant cell is a fungus, bacterium or insect cell line. It is an even further object of this invention that the recombinant fungus is a *Saccharomyces* spp., *Pichia* spp., or *Kluyveromyces* spp.; and more specifically, *S. cerevisiae, Pichia pastoris, Pichia methanolica*, or *Kluyveromyces lactis*. Alternatively, it is an object of this invention that the recombinant bacterium is *Escherichia coli, Bacillus subtilis*, or *Pseudomonas* spp. Alternatively, it is an object of this invention that the insect cell line is Sf9, Sf21, High Five, and S2. It is another object of this invention that the one or more sterol substrates is cholesterol; and the one or more sugar substrates are glucose or any disaccharide, oligosaccharide, or polysaccharide that is metabolized into glucose.

It is an object of this invention to have a method of producing steryl glucosides and phytosteryl glucosides by culturing a recombinant cell containing the Gtf-1 gene with one or more sterol substrates or one or more phytosterol substrates and one or more sugar substrates, and then isolating the produced steryl glucosides or phytosteryl glucosides. It is another object of this invention that the recombinant cell produces Gtf-1. It is a further object of this invention that the recombinant cell is a fungus, bacterium or insect cell line. It is an even further object of this invention that the recombinant fungus is a *Saccharomyces* spp., *Pichia* spp., and *Kluyveromyces* spp.; and more specifically, *S. cerevisiae, Pichia pastoris, Pichia methanolica*, or *Kluyveromyces lactis*. Alternatively, it is an object of this invention that the recombinant bacterium is *Escherichia coli, Bacillus subtilis*, or *Pseudomonas* spp. Alternatively, it is an object of this invention that the insect cell line is Sf9, Sf21, High Five, and S2. It is another object of this invention that the one or more phytosterol substrates are ergosterol, stigmasterol, campesterol, and β-sitosterol; and the one or more sugar substrates are glucose or any disaccharide, oligosaccharide, or polysaccharide that is metabolized into glucose.

It is an object of this invention to have a method of producing fatty-acid glucosides by culturing a recombinant cell containing the Gtf-1 gene with one or more fatty-acids and one or more sugar substrates.

It is an object of this invention to have a method of producing fatty-acid glucosides by culturing a recombinant cell containing the Gtf-1 gene with one or more fatty-acid substrates and one or more sugar substrates. It is another object of this invention that the recombinant cell produces Gtf-1.

It is an object of this invention to have a method of producing fatty-acid glucosides by culturing a recombinant cell containing the Gtf-1 gene with one or more fatty-acid substrates and one or more sugar substrates. It is another object of this invention that the recombinant cell produces Gtf-1. It is a further object of this invention that the recombinant cell is a fungus, bacterium or insect cell line.

It is an object of this invention to have a method of producing fatty-acid glucosides by culturing a recombinant cell containing the Gtf-1 gene with one or more fatty-acid substrates and one or more sugar substrates and then isolating the produced fatty acid glucosides. It is another object of this invention that the recombinant cell produces Gtf-1. It is a further object of this invention that the recombinant cell is a fungus, bacterium, or insect cell line. It is an even further object of this invention that the recombinant fungus is a *Saccharomyces* spp., *Pichia* spp., and *Kluyveromyces* spp.; and more specifically, *S. cerevisiae, Pichia pastoris, Pichia methanolica*, or *Kluyveromyces lactis*. Alternatively, it is an object of this invention that the recombinant bacterium is *Escherichia coli, Bacillus subtilis*, or *Pseudomonas* spp. Alternatively, it is an object of this invention that the insect cell line is Sf9, Sf21, High Five, and S2.

It is an object of this invention to have a method of producing fatty-acid glucosides and by culturing a recombinant cell containing the Gtf-1 gene with one or more fatty acid substrates and one or more sugar substrates, and then isolating the produced fatty-acid glucosides. It is another object of this invention that the recombinant cell produces Gtf-1. It is a further object of this invention that the recombinant cell is a fungus, bacterium or insect cell line. It is an even further object of this invention that the recombinant fungus is a *Saccharomyces* spp., *Pichia* spp., and *Kluyveromyces* spp.; and more specifically, *S. cerevisiae, Pichia pastoris, Pichia methanolica*, or *Kluyveromyces lactis*. Alternatively, it is an object of this invention that the recombinant bacterium is *Escherichia coli, Bacillus subtilis*, or *Pseudomonas* spp. Alternatively, it is an object of this invention that the insect cell line is Sf9, Sf21, High Five, and S2. It is another object of this invention that the one or more fatty-acid substrates are 17-hydroxy-oleate, other hydroxy oleates, hydroxy stearates, hydroxy palmitates, hydroxy myristates, hydroxy laureates, or triacylglycerol; and the one or more sugar substrates are glucose or any disaccharide, oligosaccharide, or polysaccharide that is metabolized into glucose.

DETAILED DESCRIPTION OF THE INVENTION

Figure 1:
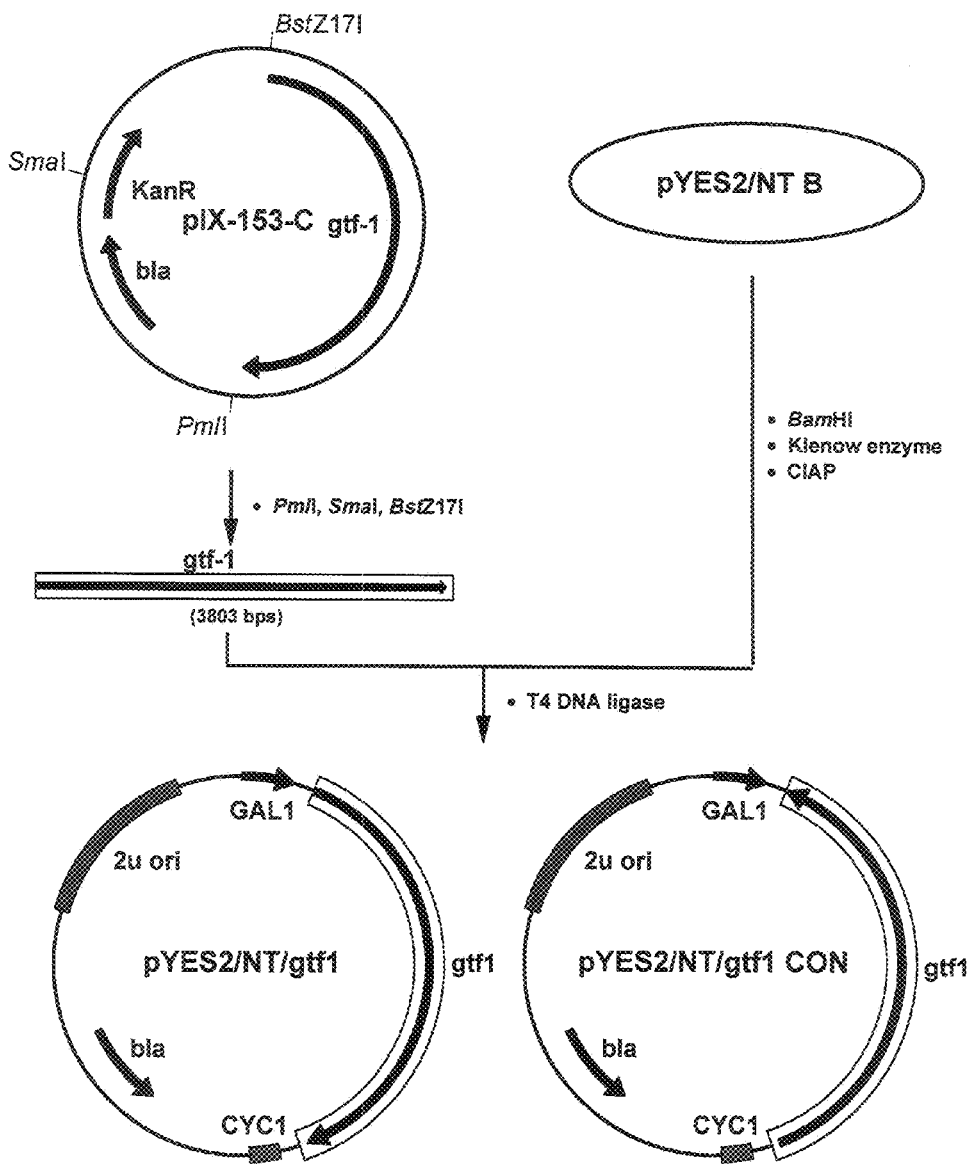
FIG. 1 is a schematic of the construction of pYES2/NT/gtf1 and pYES2/NT/gtf1CON expression vectors. Abbreviations: gtf-1, *C. bombicola* glucosyltransferase gene; KanR, aminoglycoside 3'-phosphotransferase conferring kanamycin resistance; bla, β-lactamase conferring ampicillin/carbanicillin resistance; CIAP, calf intestinal alkaline phosphatase; 2µ ori, origin-of-replication of yeast 2µ-plasmid; GAL1, yeast GAL1 promoter; CYC1, CYC1 transcription termination signal.

In this invention, the GTF-1 enzyme produced by a recombinant *Saccharomyces cereviciae* expressing *C. bombicola* gtf-1 exhibits a broad-specificity glucosyltransferase activity towards various sterols and hydroxyl fatty acids, including cholesterol, ergosterol, stigmasterol, β-sitosterol, and 17-hydroxy-oleate. The outcome of this study adds to the knowledge-base on the glycolipid metabolism of the industrially important *C. bombicola* and lays down valuable foundation for metabolic manipulation to achieve commercially viable production of glycolipids. For example, *S. cereviciae* and other fungi (such as, but not limited to, *Pichia* spp. (for example, *Pichia pastoris* and *Pichia methanolica*), and *Kluyveromyces* spp. (for example, *Kluyveromyces lactis*)), bacteria (such as, but not limited to, *Escherichia coli, Bacillus subtilis*, and *Pseudomonas* spp.), and insect cell lines (such as, but not limited to, Sf9 and Sf21 (*Spodoptera frugiperda*), High Five cell line (also known as Tn5B1-4) (*Trichoplusia ni*) and S2 (*Drosophila melanogaster*)) transformed with gtf-1 can be used to produce various steryl and phytosteryl glucosides (such as cholesteryl glucoside, ergosteryl glucoside, stigmasteryl glucoside, campesteryl glucoside, and (β-sitosterol glucoside) that are valuable as nutrition supplements, and 17-hydroxy-oleate and other fatty-acid glucosides useful as precursor for synthesis of other di- and oligo-saccharide glucosides (see, e.g., Saerens et al. 2009. *Biotechnol. J.*4:517-524; Tran et al. 2012. *Bioresource Technol.* 115:84-87) for surfactant, antimicrobial, food and cosmetic emulsifier, and other uses.

A "protein" or "polypeptide" is a chain of amino acids arranged in a specific order determined by the coding sequence in a polynucleotide encoding the protein or polypeptide. Each protein or polypeptide has a unique function.

The expression "heterologous nucleic acid sequence", "heterologous polynucleotide" or "heterologous gene" as used herein, refers to a gene or polynucleotide or nucleic acid sequence that is not in its natural environment (in other words, has been altered by the hand of man). In one embodiment a heterologous polynucleotide is a polynucleotide from one species that is introduced into another species. In another embodiment a heterologous polynucleotide can be a nucleic acid sequence joined to a regulatory element(s) e.g., a promoter, that is not found naturally associated with the polynucleotide. Heterologous genes, heterologous polynucleotides, heterologous nucleic acid sequences are typically produced using recombinant DNA techniques.

The terms "isolated", "purified", or "biologically pure" as used herein, refer to material that is substantially or essentially free from components that normally accompany the material in its native state. In one embodiment, purity and homogeneity are determined using analytical chemistry techniques such as polyacrylamide gel electrophoresis or high performance liquid chromatography. A nucleic acid that is the predominant species present in a preparation is substantially purified. In another embodiment, the term "purified" denotes that a nucleic acid or protein gives rise to essentially one band in an electrophoretic gel. Typically, isolated nucleic acids or proteins have a level of purity expressed as a range. The lower end of the range of purity for the component is about 60%, about 70% or about 80% and the upper end of the range of purity is about 70%, about 80%, about 90% or more than about 90%.

The term "nucleic acid" as used herein, refers to a polymer of ribonucleotides or deoxyribonucleotides. Typically, "nucleic acid" polymers occur in either single- or double-stranded form, but are also known to form structures comprising three or more strands. The term "nucleic acid" includes naturally occurring nucleic acid polymers as well as nucleic acids comprising known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examplary analogs include, without limitation, phosphorothioates, phosphoramidates, methyl phosphonates, chiral-methyl phosphonates, 2-O-methyl ribonucleotides, peptide-nucleic acids (PNAs). "DNA", "RNA", "polynucleotides", "polynucleotide sequence", "oligonucleotide", "nucleotide", "nucleic acid", "nucleic acid molecule", "nucleic acid sequence", "nucleic acid fragment", and "isolated nucleic acid fragment" are used interchangeably herein.

Unless otherwise indicated, a particular nucleic acid sequence also implicitly encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyino sine residues (see e.g., Batzer et al. 1991. *Nucleic Acid Res.* 19:5081; Ohtsuka et al. 1985. *J. Biol. Chem.* 260:2605-2608; and Rossolini et al. 1994. *Mol. Cell. Probes* 8:91-98).

In addition to the degenerate nature of the nucleotide codons which encode amino acids, alterations in a polynucleotide that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine or histidine, can also be expected to produce a functionally equivalent protein or polypeptide.

The term "label" as used herein, refers to a composition detectable by spectroscopic, photochemical, biochemical, immunochemical, or chemical means. Exemplary labels include $^{32}$P, fluorescent dyes, electron-dense reagents, enzymes (e.g., as commonly used in an ELISA), biotin, digoxigenin, or haptens and proteins for which antisera or monoclonal antibodies are available.

As used herein a nucleic acid "probe", oligonucleotide "probe", or simply a "probe" refers to a nucleic acid capable of binding to a target nucleic acid of complementary sequence through one or more types of chemical bonds, usually through complementary base pairing, usually through hydrogen bond formation. As used herein, a probe may include natural (i.e., A, G, C, or T) or modified bases (e.g., 7-deazaguanosine, inosine, etc.). In addition, the bases in a probe may be joined by a linkage other than a phosphodiester bond, so long as it does not interfere with hybridization. Thus, for example, probes may be peptide nucleic acids in which the constituent bases are joined by peptide bonds rather than phosphodiester linkages. It will be understood by one of skill in the art that probes may bind target sequences lacking complete complementarity with the probe sequence depending upon the stringency of the hybridization conditions. In one embodiment, probes are directly labeled as with isotopes, chromophores, lumiphores, chromogens, etc. In another embodiment probes are indirectly labeled e.g., with biotin to which a streptavidin complex may later bind. By assaying for the presence or absence of the probe, one can detect the presence or absence of the select sequence or subsequence. Thus, a probe is set of polynucleotides that can bind, either covalently, through a linker or a chemical bond, or noncovalently, through ionic, van der Waals, electrostatic, or hydrogen bonds, to a label such that the presence of the probe may be detected by detecting the presence of the label bound to the probe.

The term "primer" as used herein, refers to short nucleic acids, typically a DNA oligonucleotide of at least about 15 nucleotides in length. In one embodiment, primers are annealed to a complementary target DNA strand by nucleic acid hybridization to form a hybrid between the primer and the target DNA strand. Annealed primers are then extended along the target DNA strand by a DNA polymerase enzyme. Primer pairs can be used for amplification of a nucleic acid sequence, e.g., by the polymerase chain reaction (PCR) or other nucleic-acid amplification methods known in the art.

PCR primer pairs are typically derived from a known sequence, for example, by using computer programs intended for that purpose such as Primer (Version 0.5©1991, Whitehead Institute for Biomedical Research, Cambridge, Mass.). One of ordinary skill in the art will appreciate that the specificity of a particular probe or primer increases with its length. Thus, for example, a primer comprising 20 consecutive nucleotides of a promoter complex sequence will anneal to a particular sequence with a higher specificity than a corresponding primer of only 15 nucleotides. Thus, in one embodiment, greater specificity of a nucleic acid primer or probe is attained with probes and primers selected to comprise 20, 25, 30, 35, 40, 50 or more consecutive nucleotides of a selected sequence.

Nucleic acid probes and primers are readily prepared based on the nucleic acid sequences disclosed herein. Methods for preparing and using probes and primers and for labeling and guidance in the choice of labels appropriate for various purposes are discussed, e.g., in Sambrook et al., *Molecular Cloning, A Laboratory Manual* 2nd ed. 1989, Cold Spring Harbor Laboratory; and *Current Protocols in Molecular Biology*, Ausubel et al., eds., 1994—current, John Wiley & Sons). The term "recombinant" when used with reference, e.g., to a cell, or nucleic acid, protein, or vector, indicates that the cell, organism, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant or wild-type) form of the cell or express native genes that are otherwise abnormally expressed, over-expressed, under-expressed or not expressed at all.

The terms "transgenic", "transformed", "transformation", "transformed" and "transfection" are similar in meaning to "recombinant". "Transformation", "transgenic", and "transfection" refers to the transfer of a polynucleotide into the genome of a host organism or cell. Such a transfer of polynucleotides can result in genetically stable inheritance of the polynucleotides or in the polynucleotides remaining extra-chromosomally (not integrated into the chromosome of the cell). Genetically stable inheritance may potentially require the transgenic organism or cell to be subject for a period of time to one or more conditions which require the transcription of some or all of transferred polynucleotide in order for the transgenic organism or cell to live and/or grow under those conditions. Polynucleotides that are transformed into a cell but are not integrated into the host's chromosome remain as an expression vector within the cell. Host organisms or cells containing the recombinant polynucleotide can be referred to as "transgenic" or "transformed" organisms or cells or simply as "transformants", as well as recombinant organisms or cells.

A method of selecting an isolated polynucleotide that affects the level of expression of a polypeptide in a virus or in a host cell (eukaryotic, such as plant, yeast, fungi, or algae; prokaryotic, such as bacteria) may include the steps of: constructing an isolated polynucleotide of the present invention; introducing the isolated polynucleotide into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

An "expression cassette" as used herein, refers to a nucleic acid construct, typically generated recombinantly or synthetically, which comprises a series of specified nucleic acid elements that permit transcription of a particular nucleic acid in a host cell.

Typically, an "expression cassette" is part of an "expression vector". An expression vector or simply a "vector", as used herein, refers to nucleic acid capable of replicating in a selected host cell or organism. An expression vector can replicate as an autonomous structure, or alternatively can integrate into the host cell chromosomes or the nucleic acids of an organelle, and thus replicate along with the host cell genome. Thus, an expression vector are polynucleotides capable of replicating in a selected host cell, organelle, or organism, e.g., a plasmid, virus, artificial chromosome, nucleic acid fragment, and for which certain genes on the expression vector are transcribed and translated into a polypeptide or protein within the cell, organelle or organism; or any suitable construct known in the art, which comprises an "expression cassette".

The term "capable of hybridizing under stringent hybridization conditions" as used herein, refers to annealing a first nucleic acid to a second nucleic acid under stringent hybridization conditions (defined below). In one embodiment, the first nucleic acid is a test sample, and the second nucleic acid is the sense or antisense strand of a nucleic acid of interest. Hybridization of the first and second nucleic acids is conducted under standard stringent conditions, e.g., high temperature and/or low salt content, which tend to disfavor hybridization of dissimilar nucleotide sequences.

Any expression vector containing the polynucleotides described herein operably linked to a promoter is also covered by this invention. A polynucleotide sequence is operably linked to an expression control sequence(s) (e.g., a promoter and, optionally, an enhancer) when the expression control sequence controls and regulates the transcription and translation of that polynucleotide sequence. An expression vector is a replicon, such as plasmid, phage or cosmid, and which contains the desired polynucleotide sequence operably linked to the expression control sequence(s). The promoter may be similar or identical to a viral, phage, bacterial, yeast, insect, plant, or mammalian promoter. Similarly, the enhancer may be the sequences of an enhancer from virus, phage, bacteria, yeast, insects, plants, or mammals.

The term "operably linked" refers to the association of two or more nucleic acid fragments on a single polynucleotide so that the function of one is affected by the other. For example, a promoter is operably linked with a coding sequence so that the promoter is capable of affecting the expression of that coding sequence (i.e., that the coding sequence is under the transcriptional control of the promoter). Coding sequences can be operably linked to regulatory sequences in sense or antisense orientation. When a promoter is operably linked to a polynucleotide sequence encoding a protein or polypeptide, the polynucleotide sequence should have an appropriate start signal (e.g., ATG) in front of the polynucleotide sequence to be expressed. Further, the sequences should be in the correct reading frame to permit transcription of the polynucleotide sequence under the control of the expression control sequence and, translation of the desired polypeptide or protein encoded by the polynucleotide sequence. If a gene or polynucleotide sequence that one desires to insert into an expression vector does not contain an appropriate start signal, such a start signal can be inserted in front of the gene or polynucleotide sequence. In addition, a promoter can be operably linked to a RNA gene encoding a functional RNA.

A "promoter" is an expression control sequence and is capable of controlling the expression of a coding sequence or functional RNA. In general, a coding sequence is located 3' to a promoter sequence. The promoter sequence comprises of proximal and more distal upstream elements, the latter elements often referred to as enhancers. Accordingly, an "enhancer" is a nucleotide sequence that can stimulate promoter activity and may be an innate element of the promoter or a heterologous element inserted to enhance the level or tissue-specificity of a promoter. Promoters may be derived in their entirety from a native gene or be composed of different elements derived from different promoters found in nature, or even synthetic nucleotide segments. It is understood by those skilled in the art that different promoters may direct the expression of a gene in different tissues or cell types, or at different stages of development, or in response to different environmental conditions. Promoters that cause a polynucleotide to be expressed in most cell types at most times are commonly referred to as "constitutive promoters". Constitutive promoters for *S. cerevisiae* include, but are not limited to, CYC, ADH, STE5, PGK, GPD, CLB, AOX1, HIS4, and TEF promoters. "Inducible promoters" are promoters that cause a polynucleotide to be expressed under specific conditions such as, but not limited to, in specific tissue, at specific stages of development, or in response to specific environmental conditions, e.g., wounding of tissue or presence or absence of a particular compound. Non-limiting examples of inducible promoters for *S. cerevisiae* include MET25, GAL1, LacZ, and K1ADH4. Other examples of inducible promoters are those for the heat shock, alcohol dehydrogenase, and glucocorticoid response element genes that are activated by heat, alcohol and steroid hormones respectively. It is further recognized that because in most cases the exact boundaries of regulatory sequences have not been completely defined, nucleic acid fragments of different lengths may have identical promoter activity. In addition, promoters for bacteria and insect cell-lines are well-known to of ordinary skill in the art. For example, examples of bacterial promoters include promoters capable of recognizing the T4, T3, Sp6 and T7 polymerases, the $P_R$ and $P_L$ promoters of bacteriophage lambda, the trp, recA, heat shock, lacUV5, tac, lpp-lacSpr, phoA, and lacZ promoters of *E. coli*, promoters of *B. subtilis*, the promoters of the bacteriophages of *Bacillus* spp., the int promoter of bacteriophage lambda, the bla promoter of pBR322, and the CAT promoter of the chloramphenicol acetyl transferase gene. Prokaryotic promoters have been reviewed by Glick, *Ind. Microbiol.* 1:277 (1987), Watson, et al., *Molecular*

*Biology of the Gene*, 4th ed. (Benjamin Cummins 1987), and by Ausubel, et al. (1994). Non-limiting examples of promoters that can be used in insect cell lines include HSP70, HSP90, HSP60, HSP27, HSP72, HSP73, HSP25, HSP28, ubiquitin promoter, and metallothionein promoter. Other examples of promoters for insect cell lines are discussed in U.S. App. Pub. 20100167389 and U.S. App. Pub. 20110203010.

The following terms are used to describe the sequence relationships between two or more nucleic acids or polynucleotides: "reference sequence", "comparison window", "sequence identity", "percentage of sequence identity", and "substantial identity". A reference sequence is a defined sequence used as a basis for a sequence comparison; a reference sequence may be a subset of a larger sequence, or gene sequence given in a sequence listing.

The terms "identical" or percent "identity", in the context of two or more nucleic acids or polypeptide sequences, refer to two or more sequences or subsequences that are the same or have a specified percentage of amino acid residues or nucleotides that are the same (e.g., 85% identity, 90% identity, 99%, or 100% identity), when compared and aligned for maximum correspondence over a comparison window, or designated region as measured using a sequence comparison algorithm or by manual alignment and visual inspection.

The phrase "substantially identical", in the context of two nucleic acids or polypeptides, refers to two or more sequences or subsequences that have at least about 85%, identity, at least about 86%, 87%, 88%, 89%, 90%, 91%, 92%, 93%, 94%, 95%, 96%, 97%, 98%, 99%, or 100% nucleotide or amino acid residue identity, when compared and aligned for maximum correspondence, as measured using a sequence comparison algorithm or by visual inspection. In one embodiment, the substantial identity exists over a region of the sequences that is at least about 50 residues in length. In another embodiment, the substantial identity exists over a region of the sequences that is at least about 100 residues in length. In still another embodiment, the substantial identity exists over a region of the sequences that is at least about 150 residues or more, in length. In one embodiment, the sequences are substantially identical over the entire length of nucleic acid or protein sequence.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from about 20 to about 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Natl. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., Current Protocols in Molecular Biology (Ausubel et al., eds. 1995 supplement)).

One algorithm for sequence comparison is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle, *J. Mol. Evol.* 35:351-360 (1987). The method used is similar to the method described by Higgins & Sharp, *CABIOS* 5:151-153 (1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., 1984. *Nuc. Acids Res.* 12:387-395.

Two other examples of algorithms that are suitable for determining percent sequence identity and sequence similarity are the BLAST and BLAST 2.0 algorithms, which are described in Altschul et al., *Nuc. Acids Res.* 25:3389-3402 (1977) and Altschul et al., *J. Mol. Biol.* 215:403-410 (1990), respectively. Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., 1990). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N4 and a comparison of both strands. For amino acid sequences, the BLASTP program uses as defaults a wordlength of 3, and expectation (E) of 10, and the BLOSUM62 scoring matrix (see Henikoff & Henikoff, 1989. *Proc. Natl. Acad. Sci.* USA 89:10915) alignments (B) of 50, expectation (E) of 10, M=5, N=4, and a comparison of both strands.

The BLAST algorithm also performs a statistical analysis of the similarity between two sequences (see, e.g., Karlin and Altschul, 1993. *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, or less than about 0.01, or less than about 0.001.

An indication that two nucleic acid sequences or polypeptides are substantially identical is that the polypeptide encoded by the first nucleic acid is immunologically cross reactive with the antibodies raised against the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules or their complements hybridize to each other under stringent conditions, as described below. Yet another indication that two nucleic acid sequences are substantially identical is that the same primers can be used to amplify the sequence.

The phrase "selectively hybridizes to" or "specifically hybridizes to" refers to the binding, duplexing, or hybridizing of a molecule only to a particular nucleotide sequence under stringent hybridization conditions when that sequence is present in a complex mixture (e.g., total cellular or library DNA or RNA). In general, two nucleic acid sequences are said to be "substantially identical" when the two molecules or their complements selectively or specifically hybridize to each other under stringent conditions.

The phrase "stringent hybridization conditions" refers to conditions under which a probe will hybridize to its target subsequence, typically in a complex mixture of nucleic acid, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology-Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength and pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions will be those in which the salt concentration is less than about 1.0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. For high stringency hybridization, a positive signal is at least two times background, preferably 10 times background hybridization. Exemplary high stringency or stringent hybridization conditions include: 50% formamide, 5×SSC and 1% SDS incubated at 42° C. or 5×SSC and 1% SDS incubated at 65° C., with a wash in 0.2×SSC and 0.1% SDS at 65° C. However, other high stringency hybridization conditions known in the art can be used.

Nucleic acids that do not hybridize to each other under stringent conditions are still substantially identical if the polypeptides that they encode are substantially identical. This situation can occur, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency.

This invention utilizes routine techniques in the field of molecular biology. Basic texts disclosing the general methods of use in this invention include Sambrook et al., *Molecular Cloning—A Laboratory Manual* (2nd Ed.), Vol. 1-3, Cold Spring Harbor Laboratory, Cold Spring Harbor, N.Y. (1989); Kriegler, *Gene Transfer and Expression: A Laboratory Manual* (1990); and Ausubel et al. (eds.), *Current Protocols in Molecular Biology* (1994). Unless otherwise noted, technical terms are used according to conventional usage. Definitions of common terms in molecular biology maybe found in e.g., Benjamin Lewin, *Genes IX*, published by Oxford University Press (2007) (ISBN 0763740632); Krebs, et al. (eds.), *The Encyclopedia of Molecular Biology*, published by Blackwell Science Ltd. (1994) (ISBN 0-632-02182-9); and Robert A. Meyers (ed.), *Molecular Biology and Biotechnology: a Comprehensive Desk Reference*, published by VCH Publishers, Inc. (1995) (ISBN 1-56081-569-8).

For nucleic acids, sizes are given in either kilobases (kb) or base pairs (bp). Estimates are typically derived from agarose or acrylamide gel electrophoresis, from sequenced nucleic acids, or from published DNA sequences. For proteins, sizes are given in kilodaltons (kDa) or amino acid residue numbers. Proteins sizes are estimated from gel electrophoresis, from sequenced proteins, from derived amino acid sequences, or from published protein sequences.

Oligonucleotides and polynucleotides that are not commercially available can be chemically synthesized e.g., according to the solid phase phosphoramidite triester method first described by Beaucage and Caruthers, *Tetrahedron Letts.* 22:1859-1862 (1981), or using an automated synthesizer, as described in Van Devanter et al., *Nucleic Acids Res.* 12:6159-6168 (1984). Other methods for synthesizing oligonucleotides and polynucleotides are known in the art. Purification of oligonucleotides is by either native acrylamide gel electrophoresis or by anion-exchange HPLC as described in Pearson & Reanier, *J. Chrom.* 255:137-149 (1983).

The sequence of the cloned genes and synthetic oligonucleotides can be verified after cloning using, e.g., the chain termination method for sequencing double-stranded templates of Wallace et al., *Gene* 16:21-26 (1981). Using machines for sequencing DNA or RNA is known in the art field.

A "cell" includes prokaryotic cells, eukaryotic cells, viruses, fungi, and other similar organisms. Bacteria are an example of prokaryotic cells. Plants, algae, mammals, birds, fish, reptiles, amphibians are examples of eukaryotic organisms that have cells.

Having now generally described this invention, the same will be better understood by reference to certain specific examples and drawings, which are included herein only to further illustrate the invention and are not intended to limit the scope of the invention as defined by the claims. The examples and drawings describe at least one, but not all embodiments, of the inventions claimed. Indeed, these inventions may be embodied in many different forms and should not be construed as limited to the embodiments set forth herein; rather, these embodiments are provided so that this disclosure will satisfy applicable legal requirements.

EXAMPLE 1

Cloning of gtf-1

*Candida bombicola* NRRL Y-17069 is obtained from ARS Culture Collection (NCAUR, Peoria, Ill.) and *Candida bombicola* ATCC 22214 is obtained from ATCC (Manassas, Va.). Genomic DNA is isolated using YeaStar Genomic DNA Kit (Zymo Research, Irvine, Calif.) according to manufacturer's instructions. PCR cloning techniques described in Solaiman 2000, *Biotechnol. Lett.* 22:789-794 and Solaiman and Ashby, 2005, *Curr. Microbiol.* 50:329-333 are adopted for cloning gtf-1 from *C. bombicola*. Two primers, CL-V-114L1 (SEQ ID NO: 1) and CL-V-114R2 (SEQ ID NO: 2), are designed based on the conserved regions of the amino acid sequences of UDP-glucose:sterol glucosyltransferases of *S. cerevisiae* (gi6323218), *P. pastoris* (gi4768597) and *C. albicans* (gi4768599). The primers are purchased from Sigma Genosys (Woodlands, Tex.). PCR is performed on a GeneAmp PCR System 9700 (Applied Bio systems, Forster City, Calif.) using thermal cycling programs appropriate for the specific thermo-tolerant DNA polymerase and primers and according to manufacturer's instructions.

Initially, an approximately 700 bp PCR product, termed VIII 88-1 fragment, is successfully obtained from *C. bombicola* genomic DNA using CL-V-114L1 and CL-V-114R2 primers. Using chromosomal DNA walking technique (see Solaiman 2000; and Solaiman and Ashby, 2005) and Walking SpeedUp Kit (Seegene, Rockville, Md.) according to manufacturer's instructions, the VIII 88-1 fragment successfully serves as a "bridgehead" for the cloning of the entire 3.8 kb *C. bombicola* gft-1. Next the DNA sequence of the amplicon is determined using Applied Biosystems 3130 Genetic Analyzer (Foster City, Calif.). The DNA sequence is in SEQ ID NO: 3; the amino acid sequence is in SEQ ID NO: 4 (GenBank Accession No. FJ231291). The sequence is analyzed using Clone Manager 9 Professional program (Scientific & Educational Software, Cary, N.C.). BLASTP analysis (NCBI) of the translated sequence of gtf-1 (termed GTF-1) detects three conserved domains. A Pleckstrin homology (PH) domain is identified at the amino-terminal which is usually associated with membrane-targeting of protein or specific lipid binding by enzyme. In the middle of GTF-1 is a GRAM conserved domain found in various glucosyltransferases, lipid phosphatases and some membrane-associated proteins. The most prominent feature, located in the carboxyl-terminal half of GTF-1, is a UDP-glucoronosyl and UDP-glucosyl transferase-associated conserved domain. The identification of these three conserved domains strongly indicates that GTF-1 is a membrane-bound enzyme possessing lipid binding and glucosyltransferase activities, which are properties needed for glycolipid (such as sophorolipid) synthesis.

BLASTP results also identifies two closely matched orthologs of the GTF-1. One is a putative *Yarrowia lipolytica* UDP-glucose:sterol glucosyltransferase (product YALI0D18403p of GenBank sequence gi:199425822), and the second is an experimentally verified sterol 3-beta-glucosyltransferase of *Yarrowia lipolytica* (gi:73619418). The N-terminal regions of the three proteins have 38-40% identities (53% positives), while the C-terminal regions have a match of 54% identities (70% positives). The lipid or membrane-binding properties, which is attributed to the N-terminal PH domain, of GTF-1 and the *Yarrowia lipolytica* proteins are marginally similar, while their glucosyltransferase activities inherent to the C-terminal UDP-glucosyltransferase domain are more closely linked.

EXAMPLE 2

Construction of *Saccharomyces cerevisiae* Clones for gft-1 Expression

After the entire nucleotide sequence of gtf-1 is assembled via the combined PCR and genomic DNA walking techniques detailed in Example 1, the gtf-1 gene is then amplified from *C. bombicola* genome using GeneAmp PCR System 9700 (Applied Biosystems, Foster City, Calif.) using thermal cycling programs appropriate for the thermo-tolerant DNA polymerase and the following primers: CL9-102F1 (5'-AAG-GATATCTCTACCAATCAATTGAGGCTG-3'; SEQ ID NO: 7); CL9-102R1 (5'-ACTCCTAGGCTGGCCATGGATGT-GTCTG-3'; SEQ ID NO: 8); CL9-110F2A (5'-ACGGAA-GAAGGTGCGGATTC-3' SEQ ID NO: 9); CL9-110R2A (5'-CTCGCGAATGAAAGAATAAC-3' SEQ ID NO: 10); CL9-102F3 (5'-AGAGTTTCGAGAGATCGCTG-3'; SEQ ID NO: 11); and CL9-102R3 (5'-ACTGCGGCCGCATGAT-CACACTGATACGTCA-3'; SEQ ID NO: 12)) and according to manufacturer's instructions. The gtf-1 gene (3.7 kb) is amplified in sections to minimize mis-incorporation of nucleotides during the amplification process. The final amplicon is de-phosphorylated and ligated into a pT7Blue-3 vector (Invitrogen, Carlsbad, Calif.) to yield pIX-153-C (FIG. 1). The plasmid, pIX-153-C is then transformed into competent *Escherichia coli* DH5α. The transformed *E. coli* are grown and maintained in liquid or solid (1.2-1.5% w/v of agar) Luria medium (1% w/v tryptone, 0.5% w/v yeast extract, 0.5% w/v NaCl) with kanamycin (35 μg/ml) and carbenicillin (50 μg/ml) at 37° C., with 250 rpm orbital-shaking for the liquid cultures. Plasmids in *E. coli* transformants are isolated by using a GenElute Miniplasmid Kit (Sigma Aldrich, St. Louis, Mo.) for subsequent restriction analysis. The purified plasmid, pIX-153-C, is sequenced using GeneAmp PCR System 9700 (Applied Biosystems, Foster City, Calif.) according to manufacturer's instructions, to confirm the identity of the cloned gtf-1.

The coding sequence of gtf-1 is excised from purified pIX-153-C by triple restriction digestion using endonucleases PmlI, SmaI and BstZ17I (New England Biolabs, Ipswich, Mass.) according to the supplier's instructions. The restriction enzyme digested oligonucleotides undergo electrophoretic separation on an agrose gel. A 3.8-kb digestion fragment flanked by PmlI and BstZ17I sites and containing the gtf-1 coding sequence is purified from the agarose gel using Zymoclean Gel DNA Recovery Kit (Zymo Research, Orange, Calif.). Separately, pYES2/NT-B shuttle vector (Invitrogen, Carlsbad, Calif.) is linearized with BamHI, blunt-ended with DNA Polymerase Klenow fragment, and dephosphorylated with calf-intestinal alkaline phosphatase (all according to manufacturer's instructions). The purified 3.8 kb gtf-1 is ligated into the linearized pYES2/NT-B to obtain pYES2/NT/gft1 and pYES2/NT/gft1CON (FIG. 1). The recombinant plasmids, pYES2/NT/gft1 and pYES2/NT/gft1CON, are transformed into and are maintained in *E. coli* as described above. The nucleotide sequence and the orientation of gtf1 in the two plasmids, pYES2/NT/gft1 and pYES2/NT/gft1CON, are experimentally verified by sequence determination as described above.

*S. cerevisiae* strain INVSc1 (genotype: his3Δ1/his3Δ1 leu2/leu2 trp1-289/trp1-289 ura3-52/ura3-52; phenotype: His⁻, Leu⁻, Trp⁻, Ura⁻)(Invitrogen, Carlsbad, Calif.) are made competent for transformation by using an S. c. Easy-Comp Transformation Kit (Invitrogen, Carlsbad, Calif.). The competent *S. cerevisiae* strain INVSc1 are transformed with pYES2/NT/gft1, pYES2/NT/gft1CON and pYES2/NT/lacZ (a control plasmid provided by Invitrogen) individually, and the positive transformant clones are selected as colonies growing on an SC-U+Glu(2%) solid (agar) medium containing (per liter) Yeast Drop-Out minus Uracil (2 g; Sigma-Aldrich, St. Louis, Mo.), Yeast Nitrogen Base Without Amino Acids (6.7 g; Sigma-Aldrich, St. Louis, Mo.), D-(+)-glucose (or dextrose, 20 g; Sigma-Aldrich, St. Louis, Mo.) and Bacteriological Agar (20 g; Sigma-Aldrich, St. Louis, Mo.) according to the protocol supplied by the vendor.

All three plasmids transformed INVSc1 with a high transformation frequency, resulting in the appearance of numerous transformants on the SC-U+Glu(2%) selection agar-medium plates. In contrast, a mock transformation of INVSc1 without an added plasmid does not produce any colony on the selection plate, indicating that the clones from the plasmid-transformed *S. cereviciae* are genuine recombinants containing pYES2/NT-based plasmids expressing URA3 gene needed by INVSc1 to grow on the selection medium. Five colonies are randomly picked and separately grow in SC-U+Glu(2%) medium (without agar) at 30° C. and 250 rpm for 18 hours from each of the three *S. cereviciae* transformants (i.e., pYES2/NT/gft1, pYES2/NT/gft1CON, and pYES2/NT/lacZ) for long-term storage. Sterile glycerol is added to the cultures to a 15% (v/v) final concentration. The cultures are then stored in a −80° C. freezer.

EXAMPLE 3

Quantitative RT-PCR Assay of gft-1 Expression in *S. cerevisiae*

The expression of gtf-1 cloned into *S. cerevisiae* via the yeast vector pYES2/NT B is determined using qRT-PCR method. *S. cerevisiae* harboring the expression vector pYES2/NT/lacZ is used as the negative control. *S. cerevisiae* INVSc1 [pYES2/NT/gft1] and INVSc1 [pYES2/NT/lacZ] are streaked on SC-U+Glu(2%) agar solid-medium plates and grown for 2 days at 30° C. Individual colonies are picked to inoculate 15 ml of SC-U+Raf(2%) which contains, per liter, Yeast Drop-Out Minus Uracil (2 g; Sigma-Aldrich, St. Louis, Mo.), Yeast Nitrogen Base Without Amino Acids (6.7 g; Sigma-Aldrich, St. Louis, Mo.) and D-(+)-raffinose (20 g; Fluka (Sigma-Aldrich, St. Louis, Mo.)) in 50 ml Erlenmeyer flasks. One set of cultures are grown 18-20 hours at 30° C. and 200 rpm, and 1-ml of these overnight (i.e., grown for ≥16 hours) cultures are further used to inoculate another set of similar medium. The two sets of cultures are returned to the incubator/shaker for another 18-20 hours growth under the same conditions. Induction of the expression of the cloned genes is initiated by adding 1.5 ml of 20% (w/v) sterile D-(+)-galactose (Sigma-Aldrich, St. Louis, Mo.) solution to each culture, and the cultures are incubated under the same conditions for an additional 6 hours. Cells are harvested by centrifugation in a Sorvall RC-5B Plus (5,000×g; 5 min; 4° C.) (ThermoFisher Scientific, Waltham, Mass.) with discard of the supernatant. The pellet is resuspended, is washed once with 0.5 ml Milli-Q H$_2$O (Millipore, Billerica, Mass.), and is pelletted again in an Eppendorf 5415R (10,000 rpm×g; 1 minute; 25° C.)(Hauppauge, N.Y.). The supernatant is discarded, and the cell pellet is thoroughly resuspended in 0.5 ml of RNAlater, an RNA stabilization reagent (Qiagen, Germantown, Md.) and stored at −80° C. Total RNA is prepared by using an RNeasy Mini Kit (Qiagen, Germantown, Md.) according to manufacturer's protocol.

Primers used for qRT-PCR reactions are designed using Primer3 (v.0.4.0) software (frodo.wi.mitedu, MIT, Boston, Mass.). Preliminary qRT-PCR on the housekeeping genes ALG9 (coding for a mannosyltransferase activity in protein amino acid glycosylation) and UBC6 (coding for a ubiquitin-protein ligase activity involved in endoplasmic reticulum-associated protein catabolic process) using primers described by Teste et al. (Teste, et al. 2009. *BMC Mol. Biol.* 10:99-113) demonstrates that the UBC6 gene displays the most consistent Ct values, and thus UBC6 is chosen as the internal control gene for quantification. The primers (Sigma-Aldrich, St. Louis, Mo.) for qRT-PCT of gtf-1 are gtf-1 B FWD (5'-GGATTCTGACGATGATGAGG-3'; SEQ ID NO: 5) and gtf-1 B REV (5'-GCTTGGGTCACTCGAAAATA-3'; SEQ ID NO: 6). cDNA synthesis is performed on an Applied Biosystems GeneAmp 9600 PCR System (Foster City, Calif.) using a SuperScript III First-Strand Synthesis SuperMix Kit (Invitrogen, Carlsbad, Calif.) according to the manufacturers' instructions. Reactions are prepared for each RNA sample using 1 μg of DNase I-treated RNA. Reactions without reverse transcriptase are used as negative controls.

qRT-PCR is carried out on a 96-well plate using a Bio-Rad iQ5 real-time PCR system (Bio-Rad, Hercules, Calif.) in a 50 μl reaction volume containing 25 μl Power SYBR Green PCR Master Mix (Life Technologies, Carlsbad, Calif.), 1.25 μl of each primer at 10 μM, 0.5 μl of cDNA, and nuclease-free water to make up the difference in volume. Thermal cycling parameters are 50° C. for 2 minutes for 1 cycle, an initial denaturation at 95° C. for 10 minutes for 1 cycle, followed by 35 cycles of 95° C. for 15 seconds and 60° C. for 1 minute. Fluorescence data are collected at the 60° C. annealing step. The final step is a dissociation curve of 95° C. for 15 seconds, 60° C. for 1 minute, 95° C. for 15 seconds, and 60° C. for 15 seconds. Results are visualized using the 7500 System SDS Software provided with the thermocycler. All qRT-PCR experiments are performed with two biological and two technical replicates in a 96-well plate. To evaluate genomic DNA contamination in the cDNA samples, "no amplification controls" (NAC, a minus-reverse transcriptase control) are included. In addition, three "no template controls" (NTC) containing all of the RT-PCR reagents except the RNA template are included in each reaction plate. To determine relative gene expression, the Ct value of the internal control gene (UBC6) is subtracted from the experimental (pYES2/NT/gft1) and the non-gft1 control (pYES2/NT/lacZ) samples. The ΔCt, ΔΔCt, and the $2^{-fx}$ values are calculated (see Liu and Ream, 2008. *Appl. Environ. Microbiol.* 74:6859-6866; Pfaffl 2001. *Nucleic Acids Res.* 29:e45).

As shown in Table 1, the Ct value of gtf-1 in pYES2/NT/gft1 is 15, whereas the Ct value of lacZ in pYES2/NT/lacZ is over 34. The large differences between the Ct values of the experimental sample (pYES2/NT/gft1) and the negative control (pYES2/NT/lacZ) indicates that the gft-1 gene is highly expressed. The Ct value of UBC6 (internal control) remains constant between the two constructs, indicating that the differences in Ct between gtf-1 and lacZ are not because of the presence of unequal amounts of RNA. Results from the real-time PCR assays thus summarily demonstrate that the gtf-1 gene is highly expressed in the recombinant S. cereviciae [pYES2/NT/gft1].

TABLE 1

The gtf-1 gene expression in yeast, calculated by ΔΔCt method

| Constructs | Average Ct | | ΔCt (gtf-1-UBC6) | ΔΔCt (gtf-1-lacZ) | Fold difference relative to lacZ |
|---|---|---|---|---|---|
| | UBC6 (internal control gene) | gtf-1 | | | |
| pYES2/NT/lacZ | 27.8 ± 0.1 | 34.6 ± 0.2 | 6.8 ± 0.2 | 0 | 1 |
| pYES2/NT/gft1 | 28.0 ± 0.4 | 15.1 ± 0.1 | −12.9 ± 0.4 | −19.7 ± 0.4 | 851708 |

EXAMPLE 4

Glucosyltransferase Activity in Recombinant S. cerevisiae

An in vitro enzyme activity assay is performed to verify the functional property of Gtf-1 expressed in the recombinant S. cereviciae [pYES2/NT/gft1]. In this plasmid, the expression of gtf-1 is regulated by a yeast GAL1 promoter that is inducible by the addition of galactose (FIG. 1). An HPLC-MS-based method is developed to assay for glucosyltransferase activity in recombinant S. cerevisiae expressing C. bombicola gft-1 gene cloned in the pYES2/NT/gft1 plasmid construct. As control samples, S. cerevisiae transformed with pYES2/NT/gft1CON and pYES2/NT/lacZ are included in the study. The growing and induction of S. cerevisiae cells is performed according to the protocol described in the manual of pYES2/NT Yeast Expression System (Invitrogen, Carlsbad, Calif.). Briefly, cells from long-term (−80° C.) storage stock cultures are streaked on Yeast Extract Peptone Dextrose (YPD) agar solid medium (1% w/v yeast extract, 2% w/v peptone, 2% w/v dextrose (D-(+)glucose), 2% w/v agar) and grown at 30° C. for 1 to 2 days. A single colony is picked to inoculate 5 ml of SC-U+Glu(2%) in a 25-ml Erlenmeyer flask. The culture is grown overnight at 30° C. and 200 rpm. A volume of the overnight culture, which is based on achieving a theoretical absorbance at 600 nm ($A_{600\ nm}$)=0.4 in the fresh culture, is added to 50 ml of SC-U+Raf(2%) medium in a 125-ml Erlenmeyer. After an overnight incubation (30° C., 200 rpm), $A_{600\ nm}$ values of the cultures are recorded. Five ml of sterile 20% (w/v) D-(+)-galactose are added to each culture to induce expression of the cloned gene, and the cells are incubated for 4 hours at 30° C., 200 rpm. Cells are then harvested by centrifugation (Sorvall RC-5B Plus centrifuge; 5,000×g; 10 min; 4° C.) (ThermoFisher Scientific, Waltham, Mass.) with the supernatant being decanted. The pelleted cells are resuspended and washed with 5 ml cold water, undergo another centrifugation using same parameters with removal of the supernatant after centrifugation, and are resuspended in a volume of a Breaking Buffer (50 mM sodium phosphate at pH 7.4; 1 mM Na-EDTA; 5% v/v glycerol; 1 mM phenylmethylsulfonylfluoride (PMSF) which is added immediately before use) in 15-mL Corex centrifugation tube to give a theoretical $A_{600\ nm}$ of 200. Cell suspension can be stored at −20° C. overnight and still retain glucosyltransferase activity. Cells are broken by sonication (Sonicator model W-385 equipped with a microtip probe; Heat-Systems, Inc., Farmingdale, N.Y.) for 10 to 15 seconds (with 30 seconds sample cooling on ice-water bath) at maximum probe-tolerant power setting. The sonicated cell suspension (SCS) is used in the reaction mixtures to assay for glycosylation activity.

The reaction mixture for glycosylation assay is largely based on that described by Saerens et al. 2011b. The following procedure is used: 10 µl of a 50 mM-lipid substrate stock solution (which is prepared in one of the following solvents: DMF (dimethylformamide), DMSO (dimethylsulfonyloxide), THF (tetrahydrofuran), ethylacetate, or ethanol) and 10 µl of a 50 mM-UDP-glucose solution (Sigma Aldrich, St. Louis, Mo.) are added to 30 µl of 50 mM potassium phosphate buffer (pH 7.5) in a 13×100 mm test tube on ice. 200 µl of the sonicated cell suspension is then added to the mixture of the two substrates. The final reaction mixture (250 µl) is incubated at 30° C. for 3 hours with frequent manual mixing (approximately every 10-15 minutes). The reaction is stopped by the addition of 200 µl of 2N HCl, followed by vigorous vortex mixing for approximately 30 to 60 seconds. The reaction mixture is extracted with 1 to 2 ml 1:1 v/v ethylether/ethylacetate mixture by vigorous vortex mixing. The tube is placed on lab bench undisturbed for phase separation to occur. Using a Hamilton syringe, the organic phase (upper layer) is carefully removed and is placed into a clean test tube (12×75 mm). The solvent is then evaporated by passing a stream of nitrogen gas over the solution, leaving a dry residue.

The dry residue is subjected to HPLC-MS analysis. The lipid substrates tested in this study are cholesterol (Alfa Aesar, Ward Hill, Mass.), ergosterol (Alfa Aesar), stigmasterol (MP Biomedicals, Solon, Ohio), β-sitosterol (MP Biomedicals), and 17-hydroxy-oleate (17-OH-oleate, prepared as described in Zerkowski and Solaiman 2006. *J. Am. Oil Chemists' Soc.* 83:621-628). HPLC-MS is conducted with an Agilent 1100 HPLC with Evaporative Light Scattering Detection and quadrupole mass spectrometry system using a Prevail C18 3µ column (2.1×150 mm, Alltech Associates, Deerfield, Ill.) operating at a flow rate of 0.2 ml/min. A gradient mobile phase is used with A) Water and B) methanol and 0.2% Acetic Acid. The gradient timetable is, 0 minutes, 20/80, A/B; 40 minutes, 0/100/50 minutes, 0/100; 51 minutes, 20/80 and 60 minutes 20/80. An electrospray ionization chamber is used with the following parameters: 200-1200 m/z, fragmentor 5 V, drying gas 10, nebulizer pressure 20, drying gas temperature 300° C., and capillary voltage 4000. In this system the lipid substrates, cholesterol and 17-OH oleate, elute at 49.5 and 10.0 minutes, respectively and the glucosyltransferase products, cholesterol glucoside and methyl 17-OH oleate glucoside, elute at 35.3 minutes and 5.8 minutes, respectively.

Recombinant S. cereviciae [pYES2/NT/lacZ] serves as a non-(gtf-1)-expressing control strain. The sugar substrate used is UDP-glucose, and the lipid substrates tested are 17-hydroxy-oleate, cholesterol, ergosterol, stigmasterol, and β-sitosterol. These selections are chosen to represent the general lipid classes of hydroxy fatty acids/esters, animal sterols, and plant sterols. As discussed supra, various solvents are used to prepare the lipid stock solutions at 50 mM concentration. It is determined that THF completely dissolves the added lipid; however, THF inhibits enzyme activity. Among all other tested solvents (i.e., DMF, DMSO, ethanol, and ethyl acetate), DMF is the best-suited solvent to prepare the lipid stock solutions with complete (or near complete) dissolution of substrate at room temperature, and without adversely impacting on enzymatic activity. However, the other solvents can be used.

Figure 2:
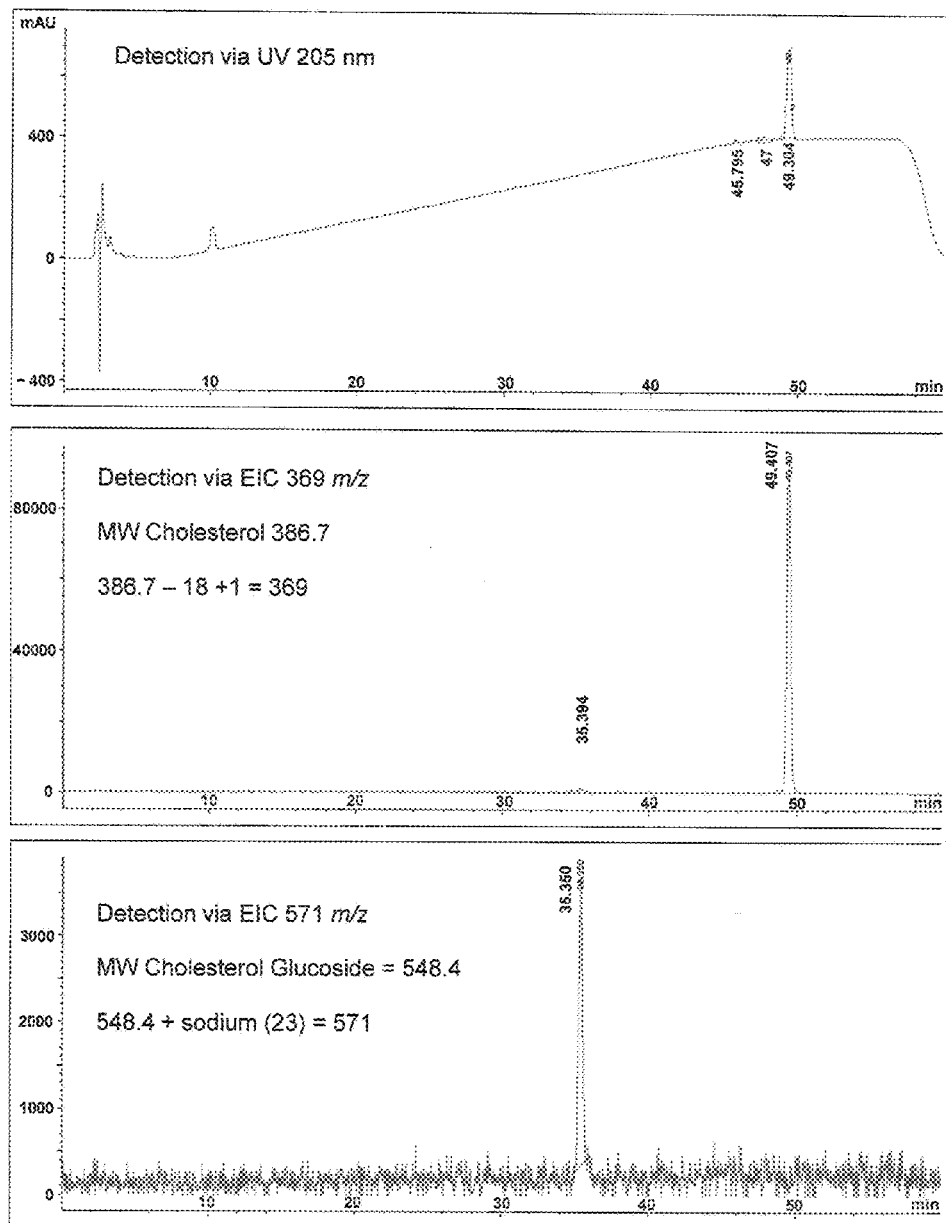
FIG. 2 shows the HPLC-MS of the products of incubation of recombinant *S. cerevisiae* [pYES2/NT/gft1] extract with cholesterol. The 571 m/z ion is only present when extract of the recombinant *S. cerevisiae* expressing the cloned gtf-1 is incubated with cholesterol, confirming that Gtf-1 is a glucosyltransferase enzyme active toward a sterol substrate.

When cell extracts of the recombinant S. cereviciae [pYES2/NT/gft1] are incubated with cholesterol, the presence of glucosyltransferase enzyme activity is confirmed by the appearance of cholesteryl glucoside at 35.3 minutes as evidenced by the appearance of a peak with a 571 m/z ion which corresponds to molecular weight of cholesteryl glucoside (548.4)+sodium (Rau et al. 2001) (FIG. 2). The 571 m/z ion (shown as an Extract Ion Chromatogram, EIC, 571 EIC m/z, in FIG. 2) is absent when the cell extracts of the control S. cerevisiae [pYES2/NT/lacZ] strain are incubated with cholesterol, confirming that Gtf-1 expressed in the S. cerevisiae [pYES2/NT/gft1] is a glucosyltransferase enzyme. Similar experiments using ergosterol, stigmasterol, and β-sitosterol as the lipid substrate give the same results, demonstrating that Gtf-1 has a broad substrate-specificity toward sterols.

Figure 3:
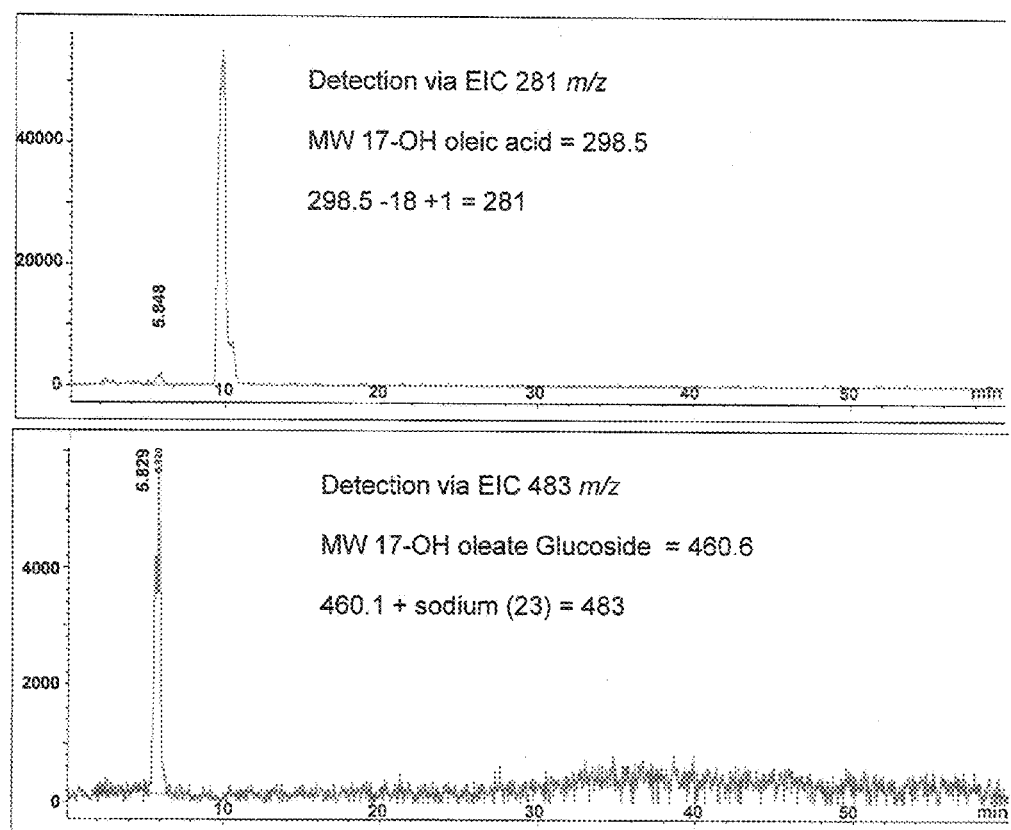
FIG. 3 shows the HPLC-MS of the products of incubation of recombinant *S. cerevisiae* [pYES2/NT/gft1] extract with 17-OH oleate. The 483 m/z ion is only present when extract of the recombinant *S. cerevisiae* expressing the cloned gtf-1 is incubated with 17-OH oleate, confirming that Gtf-1 is a glucosyltransferase enzyme with an activity toward a hydroxyl fatty acid substrate.

More importantly, when the S. cereviciae [pYES2/NT/gft1] extract is incubated with 17-OH oleate, the presence of glucosyltransferase enzyme activity is confirmed by the appearance of 17-OH oleate glucoside at 5.8 minutes as evidenced by the appearance of a peak with a 483 m/z ion which corresponds to molecular weight of 17-OH oleate glucoside (460.6)+sodium (Rau et al. 2001) (FIG. 3). The 483 m/z ion (shown as EIC 483 m/z in FIG. 3) is absent when the extract of control S. cerevisiae [pYES2/NT/lacZ] is incubated with 17-OH oleate. These results further demonstrate that the cloned C. bombicola gft-1 gene encodes a glucosyltransferase enzyme that is active towards sterols and hydroxyl fatty acids.

The cloning of gtf-1 into S. cerevisiae and obtaining functional Gtf-1 is significant. C. bombicola is industrial yeast important for the production of sophorolipids. It is now demonstrated that Gtf-1 is involved in the first step of the biosynthesis pathway of sophorolipids based on the demonstrated glycosyltransferase activity on 17-OH oleate. In addition to furthering the understanding of sophorolipid biosynthesis pathway, Gtf-1 has a broad spectrum of substrate specificity to include sterols which renders gft-1 and Gtf-1 extremely valuable for use in the commercial production of the phytosterol-glucosides with nutriceutical importance (Bouic P J D, 2002. *Drug Discovery Today* 7:775-778; Fernandes and Cabral, 2007. *Bioresour. Technol.* 98:2335-2350; Gabay et al. 2010. *Osteoarthritis & Cartilage* 18:106-116; Moreau et al. 2002. *Prog. Lipid Res.* 41:457-500; and Quílez et al. 2003. *Clin. Nutr.* 22:343-351). Furthermore, this invention covers a recombinant yeast strain expressing Gtf-1 having a broad spectrum of substrate specificity.

EXAMPLE 5

Fermentative Production of Steryl Glucosides and Fatty-Acid Glucosides Using Recombinant S. cereviciae Expressing gtf-1

Recombinant S. cereviciae [pYES2/NT/gft1] is used to produce steryl glucosides or fatty-acid glucosides by the appropriate addition of lipid and sugar substrates. The glucoside products are isolated from the fermentation culture by solvent extraction. Briefly, recombinant S. cereviciae [pYES2/NT/gft1] cells from long-term (−80° C.) storage stock cultures are streaked on Yeast Extract Peptone Dextrose (YPD) agar solid medium (1% w/v yeast extract, 2% w/v peptone, 2% w/v dextrose (D-(+)glucose), 2% w/v agar) and grown at 30° C. for 1 to 2 days. A single colony is picked to inoculate 5 ml of SC-U+Glu(2%) in a 25-ml Erlenmeyer flask. The culture is grown overnight (18-24 hours) at 30° C. and 200 rpm. The entire 5-ml overnight-culture is added as inoculum to 100 ml of SC-U+Raf(2%) medium in a 500-ml Erlenmeyer flask. The culture is then grown overnight (18-24 hours) at 30° C. and 200 rpm. The 100-ml overnight-culture is then added as inoculum to 2 liters (or optionally to 5 liters) of SC-U+Raf(2%) medium in a 3-liter (or 10-liter) fermentation vessel of a bioreactor. For fermentation of 2-liter culture in 3-liter vessel, a BioFlo III bioreactor (Eppendorf, Hauppauge, N.Y.) operating at 200-700 rpm, 30° C., and air-flow of 1-2 vessel-volume-minute is used. For the fermentation of 5-liter culture in 10-liter vessel, a BioFlo 3000 bioreactor (Eppendorf, Hauppauge, N.Y.) operating at 200-700 rpm, 30° C., and air-flow of 1-2 vessel-volume-minute is used. At 24 hours after inoculation, a pre-determined volume of sterile 20% (w/v) D-(+)-galactose which results in a final galactose-concentration of about 2% (w/v) galactose, is added to the culture to induce expression of the cloned gene. At the same time, the desired lipid substrate (i.e., sterol or fatty acid or triacylglycerol) and sugar substrate (i.e., saccharide or oligosaccharide) are added to the culture. After 24 hour fermentation, another addition of both lipid and sugar substrates is commenced, and the fermentation run is continued for another 24 hours. Two approaches are used to isolate the final lipid-glucoside products. In one approach, the culture is centrifuged in a Sorvall RC-5B Plus centrifuge (Beckman Coulter, Brea, Calif.) at 5,000×g; 10 minutes; 4° C. to pellet the cells. The cell-free, clear supernatant is lyophilized. The dried residue is then extracted with 2:1 (v/v) chloroform/ethanol solvent mixture. After removing residual solids in the extraction mixture using a Whatman #1 or #2 filter paper, the clear extract is subject to $N_2$-gas blowing to evaporate all the solvent. The dried residues constitute the desired lipid-glucoside product. In the second isolation scheme, the entire culture, including the recombinant S. cereviciae, are lyophilized. The dried residue is then extracted with 2:1 (v/v) chloroform/ethanol solvent mixture. After removing residual solids in the extraction mixture using a Whatman #1 or #2 filter paper, the clear extract is subject to $N_2$-gas blowing to evaporate all the solvent. The dried residues constitute the desired lipid-glucoside product.

The sugar substrate in this example can be glucose, or any disaccharide, oligosaccharide, or polysaccharide that is metabolized into glucose by S. cereviciae or any other recombinant cell transformed with the Gft-1 gene (gft-1). As for the lipid substrate in this example, cholesterol, ergosterol, stigmasterol, β-sitosterol, and campesterol can be used and result in the production of cholesteryl glucoside, ergosteryl glucoside, stigmasteryl glucoside, β-sitosterol glucoside, and campesteryl glucoside, respectively. The fatty acid substrate in this example can be 17-hydroxy-oleate (also referred to as 17-OH oleate) which results in the production of 17-hydroxy-oleate glucoside (as referred to as 17-OH oleate glucoside). Other fatty acids, such as but not limited to, other hydroxy oleates, hydroxy stearates, hydroxy palmitates, hydroxy myristates and hydroxy laureates, can be used. Any triacylglyerol may also be used.

Many modifications and other embodiments of the inventions set forth herein will come to mind to one skilled in the art to which these inventions pertain, having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation. All documents cited herein are incorporated by reference.

We claim:

1. A method for the production of steryl glucosides comprising culturing an isolated, recombinant cell with cholesterol and either glucose or a sugar substrate that is metabolizable into glucose; and isolating the steryl glucosides; wherein said isolated, recombinant cell comprises a heterologous polynucleotide encoding a lipid-glucosyltransferase capable of producing steryl glucosides, fatty-acid glucosides, and phytosteryl glucosides, wherein said polynucleotide has the DNA sequence of SEQ ID NO:3 or a sequence at least 90% identical to SEQ ID NO: 3, and wherein said isolated, recombinant cell produces a heterologous lipid-glucosyltransferase capable of producing steryl glucosides, fatty-acid glucosides, and phytosteryl glucosides.

2. The method of claim 1 wherein said recombinant cell is selected from the group consisting of fungi, bacteria and an insect cell line.

3. The method of claim 2 wherein said recombinant cell is selected from the group consisting of *Saccharomyces cerevisiae, Pichia pastoris, Pichia methanolica, Kluyveromyces lactis, Escherichia coli, Bacillus subtilis, Pseudomonas* spp., Sf9 insect cell line, Sf21 insect cell line, High Five insect cell line, and S2 insect cell line.

4. A method for the production of phytosteryl glucosides comprising culturing an isolated, recombinant cell with a phytosterol substrate and either glucose or a sugar substrate that is metabolizable into glucose; and isolating the phytosteryl glucosides; wherein said isolated, recombinant cell comprises a heterologous polynucleotide encoding a lipid-glucosyltransferase capable of producing steryl glucosides, fatty-acid glucosides, and phytosteryl glucosides; wherein said polynucleotide has the DNA sequence of SEQ ID NO: 3 or a sequence at least 90% identical to SEQ ID NO: 3, and wherein said isolated, recombinant cell contains a heterologous lipid-glucosyltransferase capable of producing steryl glucosides, fatty-acid glucosides, and phytosteryl glucosides.

5. The method of claim 4 wherein said phytosterol substrate is selected from the group consisting of ergosterol, stigmasterol, campesterol, and (β-sitosterol.

6. The method of claim 4 wherein said recombinant cell is selected from the group consisting of fungi, bacteria and an insect cell line.

7. The method of claim 6 wherein said recombinant cell is selected from the group consisting of *Saccharomyces cerevisiae, Pichia pastoris, Pichia methanolica, Kluyveromyces lactis, Escherichia coli, Bacillus subtilis, Pseudomonas* spp., Sf9 insect cell line, Sf21 insect cell line, High Five insect cell line, and S2 insect cell line.

8. A method for the production of fatty-acid glucosides comprising culturing an isolated, recombinant cell with a fatty-acid and either glucose or a sugar substrate that is metabolizable into glucose; and isolating the fatty-acid glucosides, wherein said isolated, recombinant cell comprises a heterologous polynucleotide encoding a lipid-glucosyltransferase capable of producing steryl glucosides, fatty-acid glucosides, and phytosteryl glucosides; wherein said polynucleotide has the DNA sequence of SEQ ID NO: 3 or a sequence at least 90% identical to SEQ ID NO: 3, and wherein said isolated, recombinant cell contains a heterologous lipid-glucosyltransferase capable of producing steryl glucosides, fatty-acid glucosides, and phytosteryl glucosides.

9. The method of claim 8, wherein said fatty-acid is selected from the group consisting of hydroxy oleates, hydroxy stearates, hydroxy palmitates, hydroxy myristates and hydroxy laureates or triacylglycerol.

10. The method of claim 8 wherein said recombinant cell is selected from the group consisting of fungi, bacteria and an insect cell line.

11. The method of claim 8 wherein said recombinant cell is selected from the group consisting of *Saccharomyces cerevisiae, Pichia pastoris, Pichia methanolica, Kluyveromyces lactis, Escherichia coli, Bacillus subtilus, Pseudomonas* spp., Sf9 insect cell line, Sf21 insect cell line, High Five insect cell line, and S2 insect cell line.

\* \* \* \* \*

SEQUENCE LISTING

<160> NUMBER OF SEQ ID NOS: 12

<210> SEQ ID NO 1
<211> LENGTH: 34
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (29)..(29)
<223> OTHER INFORMATION: n is a, c, g, or t

<400> SEQUENCE: 1
tgccatggac tagaactaga gcttayccnc aygc                           34

<210> SEQ ID NO 2
<211> LENGTH: 35
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (27)..(27)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (33)..(33)
<223> OTHER INFORMATION: n is a, c, g, or t

<400> SEQUENCE: 2
ggaataccag ctctcatagt agcaccngtn gtncc                          35

<210> SEQ ID NO 3
<211> LENGTH: 3732
<212> TYPE: DNA
<213> ORGANISM: Candida bombicola

<400> SEQUENCE: 3
atgcaggaaa cgcttttcaag ccagcagcct gacgcccagc cccagagaat atcgaactca    60
gaagagcagc aatacgatga ctccgctttc aactctgatg cagatgatga agacggtcta   120
gaaaagattc agcgcttctt cacaggtgaa tcctcagcct attatggaca ggatgatgag   180
gatttgaacg ctcgtgagcg cgaatacgta acgcaattgt taagtgaaga aggcgaggcc   240
gggttgtctg tcggcaggtt cgaaggctgg ctaggtaaaa ccgtcctgct gcagggaaag   300
atcttcataa ccaatcggta tttcctgttt tacgctcacc ttcctgtaac gaatggaact   360
cttaaggcct caccattggc taagaagtct gttaggcatt tggtaggcat tggcaaggcc   420
agctacattc gcttctggtt cgtacttcgc gcaggagcac ttctttggta cgaggaccct   480
ggcgatattt tctttccagc tggcctgctc tctctaaatt tgatgtcaga gatcagggtg   540
gtcccagagg caccagagaa gttctgcatc aaatccttaa cgggaaaagt ttacaccttc   600
aaagcagaca gcagaaatgc ggctaacgaa tgggtcaaag ccatagagaa agaaatttc    660 aaagctcgaa acaacaacac ggcacttct gtggtggttc ggatcccgct gaagaacatg   720
atttccctca agaccccttaa gcccctagac ttcgttgatg ttattgaatt tctagcgatc   780
actcaaggct ctgtcaatcc cgctgagtcc caagtgggca aattcacttt cgccttcttt   840
ggcgatcaga gaccctgaa ttccatcatt gacaggatca gcacttccac caacaacttt   900

```
gagcatcaga agggcgtcaa gttcaacacc actgcggaag gggaggagtt ggatttggct      960
cactctcaag tcggcccgt cgatgagagt gtgttcgaca ctacgcgagc gtcaaacaca     1020
gatgtgtttg aatttaaata tgttagcgac gatagggagg cggttcgctt agccggagaa    1080
gacgagactg agagcggttc tcaggtctct tctcagctga cttctgaaca ttcttcctcg    1140
ctcaatttaa gtcctatttc atctcacgga aatcggcgat cctttttcag caaatcttcg    1200
cttcgaagca gcacgttatt gcattcccgt attccgaccc gatcgggcac gccgagtaag    1260
tctccaacgc cgacagacag ctacagtcac agcaagtcaa aaaccaattt gttctccacc    1320
ttgaatgaga agcttcacaa gctaaagcat gatgactcaa agattgatct cgcgcctatc    1380
attgcaatgc caaagaagct aataccaaac ttaggcgagc aatctcacga tgtttcagat    1440
acggaagaag gtgcggattc tgacgatgat gaggagagcc aagacgacag caaaatcaat    1500
ctaaatctcc cgcaagtact cagccaaaag ttgagcatat tttcgagtga cccaagcaca    1560
gacacatcca tggccagtga ggcacaatca agccaactag atctcaactc gcttaaccag    1620
aaatttcgag aaagattcgg tttgccatcc tttgtcaatc ttctagcaga ataccagcgc    1680
tcattcaaga aacctaacga ctcatcatct tggtctggaa cttttattggt tgcgagtgat    1740
tatctttgtt tcaatcgaca aaaagtggc agctcctgcc acagaatgat cattcctttg     1800
aaagacataa tccacatcaa gaaggaacct atgcaatcct caaatcttga atttgaagtt    1860
gctgagaccg cctactcaga gttttcactt aaatttccgg aacccgccga tcgcaaagac    1920
gcagacgaca tgactcgttc agtttggcag caacaacgga caaagatga aggaaataca     1980
ctccgaggta acagcaacaa tcatgataca attgattccg aagcccaatt tttggaatat    2040
agtttgagga gcgctagact ttccacctat gagcccacgg tgacgagcca actgaagagg    2100
cggattccgc cgctcatgtt cgatcccact agcacacagt ataaggaaat attcctccaa    2160
aagcctatga aaactttgac cttttgctatg atgatgattg gaagtcgcgg agacgtgcag   2220
ccttatcttg ccttgtgtca aggcctcatg gaggagggcc ataagtgcat tattctgacg    2280
cacggggagt ttaaggaaac cgttgaagga tatgggatag agtttcgaga gatcgctggt    2340
gaccctaggg agctcatgga attgatgatc tctcacggct caataagtta ttctttcatt    2400
cgcgaggtat tgagtcactt caagagctgg ctcaaggaac tgatgaaaac ggcatggaag    2460
gccatgaaag actctggggc tgacgtcttt attgaatcgc catcgtcaat gatagggatt    2520
cacattgcag aagcgctcaa tattgcttat taccgtgcgt ttacaatgcc ttggacaaag    2580
actaaagctt atccgcaagc tttactagct cctgatcaga aacgcgctgg aaattataac    2640
gctttcaccT acgttatgta cgaccgtctt gtgtggtttg gaatttccaa gtacgtcaat    2700
aaatggcgga agcatatggg tctcccagaa acggacctag atactcttca tcaggaggat    2760
gttccatttt tgtattgtgt cagtcccact gtcttggttc cccctttgga tcaaccagat    2820
tgggttcaca cctgcggtta ttgggagctg cggccaaatg aagacaagaa agaatccggg    2880
gatgcgaaag tcgcagcatt catcaaaaaa gctcgtgaag acaaggtccc ggtaggctac    2940
ataggtttcg ggtcaataat cgtgagcgat cccgaagcaa tgacgcaaac aataatagat    3000
gcggttgacc aatcaggtgt gcgctgcgtc gtagctcgag gatggtcgtc gcgaagcact    3060
aagaagaaag ataatgacga tgaaagtgat agtactgaga agaagccgct caaccatgag    3120
aacatctgtg acgtggacag cgtcgaccac caatggctat tccccaaat ggatgtttgt     3180
gtgcaccacg gaggaagtgg cacaactggc gctagccttc gagccgggaa accgacaatt    3240
```

```
                                          -continued atcaaaccat tcttcggtga tcagtttttc tatgggcgcc gcgtagagga tcttggtgtc    3300
gggcgcaatt tgaagaagct ctctacgaag ggtctggctg aagctttgaa agagtgtact    3360
actaacaagc aaatgatacg gcaggcagat gttctcggtg agcagatccg tcacgagcat    3420
ggagtggaag aggctattct ctgcatctat cgtgaattgg catatgctaa agacgtcact    3480
attcgtcgtc gtaatgcgac tctcgaggca tcaaagaatg ggctcttttc agatccctta    3540
ggtctgctta atcctgccga actattctcg cacaaggata gaagcgaagc tgaaattttg    3600
gagaaggaag acggtggcgc cgcgaagaac aaagacaagg atcatctttg gttcacgctc    3660
ccgaaatttg gcaggcgtga ggagcaaaga caaaatcgcg atgccgatga tgaaattgac    3720
gtatcagtgt ga                                                       3732

<210> SEQ ID NO 4
<211> LENGTH: 1243
<212> TYPE: PRT
<213> ORGANISM: Candida bombicola

<400> SEQUENCE: 4

Met Gln Glu Thr Leu Ser Ser Gln Gln Pro Asp Ala Gln Pro Gln Arg
1               5                   10                  15

Ile Ser Asn Ser Glu Glu Gln Gln Tyr Asp Asp Ser Ala Phe Asn Ser
            20                  25                  30

Asp Ala Asp Asp Glu Asp Gly Leu Glu Lys Ile Gln Arg Phe Phe Thr
        35                  40                  45

Gly Glu Ser Ser Ala Tyr Tyr Gly Gln Asp Asp Glu Asp Leu Asn Ala
    50                  55                  60

Arg Glu Arg Glu Tyr Val Thr Gln Leu Leu Ser Glu Gly Glu Ala
65              70                  75                  80

Gly Leu Ser Val Gly Arg Phe Glu Gly Trp Leu Gly Lys Thr Val Leu
                85                  90                  95

Leu Gln Gly Lys Ile Phe Ile Thr Asn Arg Tyr Phe Leu Phe Tyr Ala
            100                 105                 110

His Leu Pro Val Thr Asn Gly Thr Leu Lys Ala Ser Pro Leu Ala Lys
        115                 120                 125

Lys Ser Val Arg His Leu Val Gly Ile Gly Lys Ala Ser Tyr Ile Arg
    130                 135                 140

Phe Trp Phe Val Leu Arg Ala Gly Ala Leu Leu Trp Tyr Glu Asp Pro
145             150                 155                 160

Gly Asp Ile Phe Phe Pro Ala Gly Leu Leu Ser Leu Asn Leu Met Ser
                165                 170                 175

Glu Ile Arg Val Val Pro Glu Ala Pro Glu Lys Phe Cys Ile Lys Ser
            180                 185                 190

Leu Thr Gly Lys Val Tyr Thr Phe Lys Ala Asp Ser Arg Asn Ala Ala
        195                 200                 205

Asn Glu Trp Val Lys Ala Ile Glu Lys Glu Ile Phe Lys Ala Arg Asn
    210                 215                 220

Asn Asn Thr Ala Pro Ser Val Val Arg Ile Pro Leu Lys Asn Met
225             230                 235                 240

Ile Ser Leu Lys Thr Leu Lys Pro Leu Asp Phe Val Asp Val Ile Glu
                245                 250                 255

Phe Leu Ala Ile Thr Gln Gly Ser Val Asn Pro Ala Glu Ser Gln Val
            260                 265                 270

Gly Lys Phe Thr Phe Ala Phe Gly Asp Gln Lys Thr Leu Asn Ser
        275                 280                 285
```

```
Ile Ile Asp Arg Ile Ser Thr Ser Thr Asn Asn Phe Glu His Gln Lys
290                 295                 300
Gly Val Lys Phe Asn Thr Thr Ala Glu Gly Glu Leu Asp Leu Ala
305                 310                 315                 320
His Ser Gln Val Gly Pro Val Asp Glu Ser Val Phe Asp Thr Thr Arg
                    325                 330                 335
Ala Ser Asn Thr Asp Val Phe Glu Phe Lys Tyr Val Ser Asp Asp Arg
                    340                 345                 350
Glu Ala Val Arg Leu Ala Gly Glu Asp Glu Thr Glu Ser Gly Ser Gln
                355                 360                 365
Val Ser Ser Gln Leu Thr Ser Glu His Ser Ser Ser Leu Asn Leu Ser
370                 375                 380
Pro Ile Ser Ser His Gly Asn Arg Arg Ser Phe Phe Ser Lys Ser Ser
385                 390                 395                 400
Leu Arg Ser Ser Thr Leu Leu His Ser Arg Ile Pro Thr Arg Ser Gly
                405                 410                 415
Thr Pro Ser Lys Ser Pro Thr Pro Thr Asp Ser Tyr Ser His Ser Lys
                420                 425                 430
Ser Lys Thr Asn Leu Phe Ser Thr Leu Asn Glu Lys Leu His Lys Leu
            435                 440                 445
Lys His Asp Asp Ser Lys Ile Asp Leu Ala Pro Ile Ile Ala Met Pro
        450                 455                 460
Lys Lys Leu Ile Pro Asn Leu Gly Glu Gln Ser His Asp Val Ser Asp
465                 470                 475                 480
Thr Glu Glu Gly Ala Asp Ser Asp Asp Glu Glu Ser Gln Asp Asp
                    485                 490                 495
Ser Lys Ile Asn Leu Asn Leu Pro Gln Val Leu Ser Gln Lys Leu Ser
                500                 505                 510
Ile Phe Ser Ser Asp Pro Ser Thr Asp Thr Ser Met Ala Ser Glu Ala
                515                 520                 525
Gln Ser Ser Gln Leu Asp Leu Asn Ser Leu Asn Gln Lys Phe Arg Glu
            530                 535                 540
Arg Phe Gly Leu Pro Ser Phe Val Asn Leu Leu Ala Glu Tyr Gln Arg
545                 550                 555                 560
Ser Phe Lys Lys Pro Asn Asp Ser Ser Ser Trp Ser Gly Thr Leu Leu
                565                 570                 575
Val Ala Ser Asp Tyr Leu Cys Phe Asn Arg Gln Lys Ser Gly Ser Ser
            580                 585                 590
Cys His Arg Met Ile Ile Pro Leu Lys Asp Ile Ile His Ile Lys Lys
        595                 600                 605
Glu Pro Met Gln Ser Ser Asn Leu Glu Phe Glu Val Ala Glu Thr Ala
    610                 615                 620
Tyr Ser Glu Phe Ser Leu Lys Phe Pro Glu Pro Ala Asp Arg Lys Asp
625                 630                 635                 640
Ala Asp Asp Met Thr Arg Ser Val Trp Gln Gln Arg Thr Lys Asp
                645                 650                 655
Glu Gly Asn Thr Leu Arg Gly Asn Ser Asn Asn His Asp Thr Ile Asp
            660                 665                 670
Ser Glu Ala Gln Phe Leu Glu Tyr Ser Leu Arg Ser Ala Arg Leu Ser
        675                 680                 685
Thr Tyr Glu Pro Thr Val Thr Ser Gln Leu Lys Arg Arg Ile Pro Pro
690                 695                 700
```

-continued

Leu Met Phe Asp Pro Thr Ser Thr Gln Tyr Lys Glu Ile Phe Leu Gln
705                 710                 715                 720

Lys Pro Met Lys Thr Leu Thr Phe Ala Met Met Met Ile Gly Ser Arg
            725                 730                 735

Gly Asp Val Gln Pro Tyr Leu Ala Leu Cys Gln Gly Leu Met Glu Glu
                740                 745                 750

Gly His Lys Cys Ile Ile Leu Thr His Gly Glu Phe Lys Glu Thr Val
                755                 760                 765

Glu Gly Tyr Gly Ile Glu Phe Arg Glu Ile Ala Gly Asp Pro Arg Glu
            770                 775                 780

Leu Met Glu Leu Met Ile Ser His Gly Ser Ile Ser Tyr Ser Phe Ile
785                 790                 795                 800

Arg Glu Val Leu Ser His Phe Lys Ser Trp Leu Lys Glu Leu Met Lys
                805                 810                 815

Thr Ala Trp Lys Ala Met Lys Asp Ser Gly Ala Asp Val Phe Ile Glu
            820                 825                 830

Ser Pro Ser Ser Met Ile Gly Ile His Ile Ala Glu Ala Leu Asn Ile
                835                 840                 845

Ala Tyr Tyr Arg Ala Phe Thr Met Pro Trp Thr Lys Thr Lys Ala Tyr
850                 855                 860

Pro Gln Ala Leu Leu Ala Pro Asp Gln Lys Arg Ala Gly Asn Tyr Asn
865                 870                 875                 880

Ala Phe Thr Tyr Val Met Tyr Asp Arg Leu Val Trp Phe Gly Ile Ser
                885                 890                 895

Lys Tyr Val Asn Lys Trp Arg Lys His Met Gly Leu Pro Glu Thr Asp
                900                 905                 910

Leu Asp Thr Leu His Gln Glu Asp Val Pro Phe Leu Tyr Cys Val Ser
            915                 920                 925

Pro Thr Val Leu Val Pro Pro Leu Asp Gln Pro Asp Trp Val His Thr
            930                 935                 940

Cys Gly Tyr Trp Glu Leu Arg Pro Asn Glu Asp Lys Lys Glu Ser Gly
945                 950                 955                 960

Asp Ala Lys Val Ala Ala Phe Ile Lys Lys Ala Arg Glu Asp Lys Val
                965                 970                 975

Pro Val Gly Tyr Ile Gly Phe Gly Ser Ile Ile Val Ser Asp Pro Glu
            980                 985                 990

Ala Met Thr Gln Thr Ile Ile Asp Ala Val Asp Gln Ser Gly Val Arg
                995                 1000                1005

Cys Val Val Ala Arg Gly Trp Ser Ser Arg Ser Thr Lys Lys Lys
    1010                1015                1020

Asp Asn Asp Asp Glu Ser Asp Ser Thr Glu Lys Lys Pro Leu Asn
    1025                1030                1035

His Glu Asn Ile Cys Asp Val Asp Ser Val Asp His Gln Trp Leu
    1040                1045                1050

Phe Pro Gln Met Asp Val Cys Val His His Gly Gly Ser Gly Thr
    1055                1060                1065

Thr Gly Ala Ser Leu Arg Ala Gly Lys Pro Thr Ile Ile Lys Pro
    1070                1075                1080

Phe Phe Gly Asp Gln Phe Phe Tyr Gly Arg Val Glu Asp Leu
    1085                1090                1095

Gly Val Gly Arg Asn Leu Lys Lys Leu Ser Thr Lys Gly Leu Ala
    1100                1105                1110

Glu Ala Leu Lys Glu Cys Thr Thr Asn Lys Gln Met Ile Arg Gln

```
        1115                1120                1125

Ala Asp Val Leu Gly Glu Gln Ile Arg His Glu His Gly Val Glu
        1130                1135                1140

Glu Ala Ile Leu Cys Ile Tyr Arg Glu Leu Ala Tyr Ala Lys Asp
        1145                1150                1155

Val Thr Ile Arg Arg Arg Asn Ala Thr Leu Glu Ala Ser Lys Asn
        1160                1165                1170

Gly Leu Phe Ser Asp Pro Leu Gly Leu Leu Asn Pro Ala Glu Leu
        1175                1180                1185

Phe Ser His Lys Asp Arg Ser Glu Ala Glu Ile Leu Glu Lys Glu
        1190                1195                1200

Asp Gly Gly Ala Ala Lys Asn Lys Asp Lys Asp His Leu Trp Phe
        1205                1210                1215

Thr Leu Pro Lys Phe Gly Arg Arg Glu Glu Gln Arg Gln Asn Arg
        1220                1225                1230

Asp Ala Asp Asp Glu Ile Asp Val Ser Val
        1235                1240

<210> SEQ ID NO 5
<211> LENGTH: 20
<212> TYPE: DNA
<213> ORGANISM: Candida bombicola

<400> SEQUENCE: 5
ggattctgac gatgatgagg                                                 20

<210> SEQ ID NO 6
<211> LENGTH: 20
<212> TYPE: DNA
<213> ORGANISM: Candida bombicola

<400> SEQUENCE: 6
gcttgggtca ctcgaaaata                                                 20

<210> SEQ ID NO 7
<211> LENGTH: 30
<212> TYPE: DNA
<213> ORGANISM: Artificial Sequence
<220> FEATURE:
<223> OTHER INFORMATION: Primer

<400> SEQUENCE: 7
aaggatatct ctaccaatca attgaggctg                                      30

<210> SEQ ID NO 8
<211> LENGTH: 28
<212> TYPE: DNA
<213> ORGANISM: Artificial Sequence
<220> FEATURE:
<223> OTHER INFORMATION: Primer

<400> SEQUENCE: 8
actcctaggc tggccatgga tgtgtctg                                        28

<210> SEQ ID NO 9
<211> LENGTH: 20
<212> TYPE: DNA
<213> ORGANISM: Artificial Sequence
<220> FEATURE:
<223> OTHER INFORMATION: Primer

<400> SEQUENCE: 9
```

```
acggaagaag gtgcggattc                                              20

<210> SEQ ID NO 10
<211> LENGTH: 20
<212> TYPE: DNA
<213> ORGANISM: Artificial Sequence
<220> FEATURE:
<223> OTHER INFORMATION: Primer

<400> SEQUENCE: 10
ctcgcgaatg aaagaataac                                              20

<210> SEQ ID NO 11
<211> LENGTH: 20
<212> TYPE: DNA
<213> ORGANISM: Artificial Sequence
<220> FEATURE:
<223> OTHER INFORMATION: Primer

<400> SEQUENCE: 11
agagtttcga gagatcgctg                                              20

<210> SEQ ID NO 12
<211> LENGTH: 31
<212> TYPE: DNA
<213> ORGANISM: Artificial Sequence
<220> FEATURE:
<223> OTHER INFORMATION: Primer

<400> SEQUENCE: 12
actgcggccg catgatcaca ctgatacgtc a                                 31
```